US011208390B2

(12) United States Patent
Hilderbrand et al.

(10) Patent No.: US 11,208,390 B2
(45) Date of Patent: Dec. 28, 2021

(54) FUNCTIONALIZED 1,2,4,5-TETRAZINE COMPOUNDS FOR USE IN BIOORTHOGONAL COUPLING REACTIONS

(71) Applicant: The General Hospital Corporation, Boston, MA (US)

(72) Inventors: Scott A. Hilderbrand, Swampscott, MA (US); Neal K. Devaraj, Boston, MA (US); Ralph Weissleder, Peabody, MA (US); Mark R. Karver, Chicago, IL (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/807,037

(22) Filed: Mar. 2, 2020

(65) Prior Publication Data

US 2020/0199085 A1 Jun. 25, 2020

Related U.S. Application Data

(60) Continuation of application No. 15/904,927, filed on Feb. 26, 2018, now Pat. No. 10,611,738, which is a division of application No. 14/437,905, filed as application No. PCT/US2013/031524 on Mar. 14, 2013, now Pat. No. 9,902,705.

(60) Provisional application No. 61/718,008, filed on Oct. 24, 2012.

(51) Int. Cl.
*C07D 257/08* (2006.01)
*C07D 401/04* (2006.01)
*C07D 403/12* (2006.01)

(52) U.S. Cl.
CPC ......... *C07D 257/08* (2013.01); *C07D 401/04* (2013.01); *C07D 403/12* (2013.01)

(58) Field of Classification Search
CPC .......................... C07D 257/08; C07D 401/04
See application file for complete search history.

(56) References Cited

U.S. PATENT DOCUMENTS

| 4,522,811 | A | 6/1985 | Eppstein et al. |
| 5,208,020 | A | 5/1993 | Chari et al. |
| 5,475,092 | A | 12/1995 | Chari et al. |
| 5,585,499 | A | 12/1996 | Chari et al. |
| 5,846,545 | A | 12/1998 | Chari et al. |
| 6,468,798 | B1 | 10/2002 | Debs et al. |
| 6,471,996 | B1 | 10/2002 | Sokoll et al. |
| 6,472,375 | B1 | 10/2002 | Hoon et al. |
| 9,902,725 | B2 | 2/2018 | Delhonnel |
| 2006/0269942 | A1 | 11/2006 | Kolb et al. |
| 2008/0181847 | A1 | 7/2008 | Robillard et al. |
| 2009/0023916 | A1 | 1/2009 | Fox et al. |
| 2011/0268654 | A1 | 11/2011 | Hilderbrand et al. |
| 2012/0034161 | A1 | 2/2012 | Robillard et al. |

FOREIGN PATENT DOCUMENTS

| CN | 102627615 | 8/2012 |
| EP | 1867638 | 12/2007 |
| EP | 2360167 | 8/2011 |
| WO | WO 2007/144200 | 12/2007 |
| WO | WO 2010/051530 | 5/2010 |
| WO | WO 2010/119389 | 10/2010 |
| WO | WO 2012/156920 | 11/2012 |

OTHER PUBLICATIONS

[Online] STN on the Web, Database CA, compound with RN-64500-02-3.
Agard et al., "A strain-promoted [3+2] azide-alkyne cycloaddition for covalent modification of biomolecules in living systems," J Am. Chem. Soc., Nov. 2004, 126(46):15046-47 (abstract only).
Balcar et al., "Reaktivität von stickstoff-heterocyclen genenüber cyclooctin als dienophile," Tetrahedron Lett., 1983, 24:1481-84 (with English abstract).
Baskin et al., "Bioorthogonal Click Chemistry: Covalent Labeling in Living Systems," QSAR Comb. Sci., Dec. 2007, 26:1211-19.
Baskin et al., "Copper-free click chemistry for dynamic in vivo imaging," Proc. Natl. Acad Sci. USA, Oct. 2007, 104:16793-97.
Baskin et al., "Copper-Free Click Chemistry: Bioorthogonal Reagents for Tagging Azides," Aldrichimica Acta., 2010, 43(1)15-23.
Best, "Click chemistry and bioorthogonal reactions: unprecedented selectivity in the labeling of biological molecules," Biochemistry, Jul. 2009, 48(28)6571-84.
Blackman et al., "Tetrazine Ligation: Fast Bioconjugation Based on Inverse-Electron-Demand Diels-Alder Reactivity," J. Am. Chem. Soc. 2008, 130:13518-19.
Cenoweth et al., "Cyclooctyne-based reagents for uncatalyzed click chemistry: A computational survey," Org. Biomol. Chem., 2009, 7:5255-58.
Chen et al., "Bioorthogonal chemistry for site-specific labeling and surface immobilization of proteins," Acc. Chem. Res., Sep. 2011, 44(9):762-73.
Devaraj et al., "Fast and Sensitive Pretargeted Labeling of Cancer Cells via Tetrazine/Trans-Cyclooctene Cycloaddition," Angew. Chem. Int. Ed. Engl., 2009, 48(38):7013-16.
Devaraj et al., "Tetrazine-Based Cycloadditions: Application to Pretargeted Live Cell Imaging," Bioconjug. Chem., 2008, 19:2297-99.
Dimandis et al., "The biotin-(strept)avidin system: principles and applications in biotechnology," Clin. Chem., May 1991, 37:625-36.
Dommerholt et al., "Readily accessible bicyclononynes for bioorthogonal labeling and three-dimensional imaging of living cells," Angew. Chem. Int. Ed., Dec. 2010, 49:9422-25.
Graziano, "Rate enhancement of Diels-Alder reactions in aqueous Solutions," J. Phys. Org. Chem., 2004, 17:100-01.
Hangauer et al., "A FRET-based Fluorogenic Phosphine for Live Cell Imaging with the Staudinger Ligation," Angew. Chem. Int. Ed Engl., 2008, 47:2394-97.

(Continued)

*Primary Examiner* — Brian E McDowell
(74) *Attorney, Agent, or Firm* — Fish & Richardson P.C.

(57) ABSTRACT

The present application relates to functionalized 1,2,4,5-tetrazine compounds. The compounds are useful in compositions and methods using bioorthogonal inverse electron demand Diels-Alder cycloaddition reactions for the rapid and specific covalent delivery of a "payload" to a ligand bound to a biological target.

15 Claims, 1 Drawing Sheet

(56) References Cited

OTHER PUBLICATIONS

Hilderbrand et al., "Rapid bioorthogonal inverse electron demand cycloadditions for biological imaging," Center for Systems Biology, Massachusetts General Hospital and Harvard Medical School, Boston, MA, Aug. 2010, 2 pages.

International Preliminary Report on Patentability in International Application No. PCT/US2013/031524, dated May 7, 2015, 6 pages.

International Search Report and Written Opinion dated Aug. 22, 2013 in international application No. PCT/US 2013/031524, 7 pages.

Jewett et al., "Rapid Cu-free click chemistry with readily synthesized biarylazacyclooctynones," J. Am. Chem. Soc., Mar. 2010, 132(11)3688-90.

Kolb et al., "Click Chemistry: Diverse Chemical Function from a Few Good Reactions," Angew. Chem. Int. Ed., Jun. 2001, 40:2004-21.

Kwart et al., "The reverse Diels-Alder or retrodiene reaction," Chem. Rev. 1968, 68:415-47.

Laughlin et al., "In vivo imaging of membrane-associated glycans in developing zebrafish," Science, May 2008, 320:664-67.

Lemieux et al., "A fluorogenic dye activated by the staudinger ligation," J. Am. Chem. Soc., 2003, 125:4708-09.

Lim et al., "Bioorthogonal Chemistry: Recent Progress and Future Directions," Chem. Commun. (Camb.), 2010, 46(10)1589-600.

Link et al., "Cell surface labeling of *Escherichia coli* via copper(I)-catalyzed [3+2] cycloaddition," J. Am. Chem. Soc., Sep. 2003, 125:11164-65.

Link et al., "Non-canonical amino acids in protein engineering," Curr. Opin. Biotechnol., 2003, 14:603-09.

Marks et al., "Strain-promoted "click" chemistry for terminal labeling of DNA," Bioconjugate Chem., Jul. 2011, 22(7)1259-63.

Neef et al, "Selective Fluorescence Labeling of Lipids in Living Cells," Angew. Chem. Int. Ed., 2009, 48:1498-500.

Ning et al., "Visualizing metabolically labeled glycoconjugates of living cells by copper-free and fast huisgen cycloadditions," Angew. Chem. Int. Ed, 2008, 47:2253-55.

Pipkorn et al., "Inverse-electron-demand Diels-Alder reaction as a highly efficient chemoselective ligation procedure: synthesis and function of a BioShuttle for temozolomide transport into prostate cancer cells," J. Pept. Sci., Mar. 2009, 15:235-41.

Prescher et al., "Chemical remodelling of cell surfaces in living animals," Nature, Aug. 2004, 430(7002):873-77.

Prescher et al., "Chemistry in living systems," Nat. Chem. Biol., Jun. 2005, 1(1):13-21.

Rideout et al., "Hydrophobic acceleration of Diels-Alder reactions," J Am. Chem. Soc., 1980, 102:7816-17.

Rostovtsev et al., "A Stepwise Huisgen Cycloaddition Process: Copper(I)-Catalyzed Regioselective "Ligation" of Azides and Terminal Alkynes," Angew. Chem. Int. Ed, Jul. 2002, 41(14):2596-2599.

Sauer et al., Umsetzungen von 1.2.4.5-Tetrazinen mit Olefinen. Zur Struktur von Dihydropyridazinen, Chem. Ber., 1965, 998:1435-45.

Saxon et al., "Cell surface engineering by a modified Staudinger reaction," Science, 2000, 287(5460):2007-10 (abstract only).

Seelig et al., "Site-specific modification of enzymatically synthesized RNA: Transcription initiation and Diels-Alder reaction," Tetrahedron Lett., Nov. 1997, 38:7729-32.

Sivakumar et al., "A fluorogenic 1,3-dipolar cycloaddition reaction of 3-azidocoumarins and acetylenes," Org. Lett., Nov. 2004, 6:4603-06.

Sletten et al., "Bioorthogonal Chemistry: Fishing for Selectivity in a Sea of Functionality," Angew. Chem. Int. Ed., 2009, 48(38):6974-98.

Sletten et al., "From Mechanism to Mouse: A Tale of Two Bioorthogonal Reactions," Acc. Chem. Res., 2011, 44(9)666-76.

Thalhammer et al., "Reaktivität einfacher offenkettiger und cyclischer dienophile bei Diels-Alder-reaktionen mit inversem elektronenbedarf," Tetrahedron Lett., 1990, 47:6851-54 (with English abstrat).

Wang et al., "Bioconjugation by Copper(I)-Catalyzed Azide-Alkyne [3+2] Cycloaddition," J. Am. Chem. Soc., Apr. 2003, 125:3192-3193.

Yousaf et al., "Diels-Alder Reaction for the Selective Immobilization of Protein to Electroactive Self-Assembled Monolayers," J. Am. Chem. Soc., 1999, 121:4286-87.

Zhou et al., "A fluorogenic probe for the copper(I)-catalyzed azide-alkyne ligation reaction: modulation of the fluorescence emission via 3(n,pi)-1(pi,pi) inversion," J. Am. Chem. Soc., Jul. 2004, 126:8862-63.

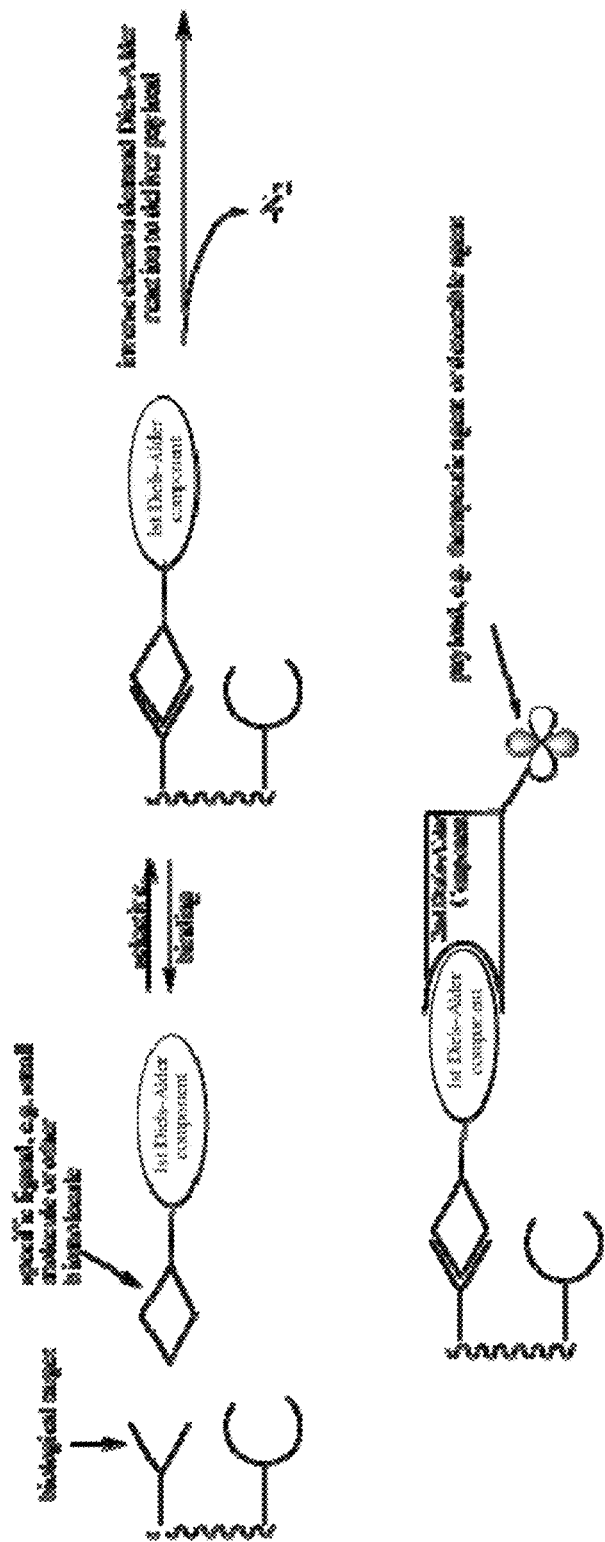

FUNCTIONALIZED 1,2,4,5-TETRAZINE COMPOUNDS FOR USE IN BIOORTHOGONAL COUPLING REACTIONS

CROSS-REFERENCE TO RELATED APPLICATIONS

This application is a continuation of U.S. patent application Ser. No. 15/904,927, filed Feb. 26, 2018, which is a divisional of U.S. patent application Ser. No. 14/437,905, filed Apr. 23, 2015 (now U.S. Pat. No. 9,902,705), which is a U.S. National Phase Application under 35 U.S.C. § 371 of International Patent Application No. PCT/US2013/031524, filed internationally on Mar. 14, 2013, which claims the benefit of U.S. Provisional Application No. 61/718,008, filed Oct. 24, 2012. The entire disclosure of each of the aforementioned related applications is hereby incorporated by reference.

STATEMENT REGARDING FEDERALLY SPONSORED RESEARCH OR DEVELOPMENT

This invention was made with Government support under Grant Nos. NHLBI U01-HL080731 and T32-CA79443 awarded by the National Institutes of Health. The Government has certain rights in the invention.

TECHNICAL FIELD

The present application relates to functionalized 1,2,4,5-tetrazine compounds. The compounds are useful in compositions and methods using bioorthogonal inverse electron demand Diels-Alder cycloaddition reactions for the rapid and specific covalent conjugation of two components, e.g., to achieve delivery of a "payload" to a ligand bound to a biological target.

BACKGROUND

Bioorthogonal reactions for coupling materials in the presence of complex biological milieu are of great interest in biology and medicine. The term refers to reactions between two molecules which, although they react with each other, do not react with the molecules present in living organisms and the functional groups present in biomolecules, and thus can be carried out without interfering with biological processes. Such reactions have become key components in a variety of applications including protein engineering, immunoassay development, and cell surface modification. See, e.g., Baskin et al., *Proc. Natl. Acad. Sci. USA*, 2007, 104, 16793-97; Best, Biochemistry, 2009, 48(28), pp. 6571-84; Chen et al., *Acc. Chem. Res.*, 2011, 44(9), 762-73; Dimandis et al., *Clin. Chem.*, 1991, 37, 625-36; Kolb et al., *Angew. Chem. Int. Ed.*, 2001, 40, 2004-21; Link et al., *Curr. Opin. Biotechnol.*, 2003, 14, 603-09; Link et al., *J. Am. Chem. Soc.*, 2003, 125, 11164-65; Prescher et al., *Nature*, 2004, 430(7002), 873-77; Prescher et al., *Nat. Chem. Biol.*, 2005, 1(1), 13-21; Lim et al., *Chem. Commun. (Camb.)*, 2010, 46(10), 1589-600; Sletten et al., *Angew. Chem. Int. Ed.*, 2009, 48(38): 6974-98; Wang et al., *J. Am. Chem. Soc.*, 2003, 12, 3192-3193. Presently, a few types of bioorthogonal reactions have been reported.

One type of reaction that has been used is the Staudinger ligation between phosphines and azides. Prescher et al., *Nature*, 2004, 430(7002), 873-77; Saxon et al., *Science*, 2000, 287(5460), 2007-10.

Another useful reaction is the [3+2] cycloaddition "click" reaction between azides and alkynes. Rostovtsev et al., *Angew. Chem. Int. Ed.*, 2002, 41(14), 2596-2599. While this reaction proceeds in the presence of copper, a copper-free variant has been developed that does not require the use of copper, involving cycloaddition of azides to a strained alkyne such as a cyclooctyne ring, a dibenzocyclooctyne ring, an azadibenzocyclooctyne ring, or a bicyclononyne (e.g., bicyclo[6.1.0]nonyne) ring. Agard et al., *J. Am. Chem. Soc.*, 2004, 126 (46), 15046-47; Baskin et al., *Aldrichimica Acta*, 2010, 43(1), 15-23; Cenoweth et al., *Org. Biomol. Chem.*, 2009, 7, 5255-58; Dommerholt et al., *Angew. Chem. Int. Ed.*, 2010, 49, 9422-25; Jewett et al., *J. Am. Chem. Soc.*, 2010, 132 (11), 3688-90; Marks et al., *Bioconjugate Chem.*, 2011, 22(7), 1259-63; Sletten et al., *Acc. Chem. Res.*, 2011, 44(9), 666-76.

Bioorthogonal "click" chemistries are widely used in chemical biology for a myriad of applications such as activity based protein profiling, crosslinking of proteins, monitoring cell proliferation, generation of novel enzyme inhibitors, monitoring the synthesis of newly formed proteins, protein target identification, and studying glycan processing. Bioorthogonal chemistry has been used, e.g., to assemble molecules in the presence of living systems such as live cells or even whole organisms. Baskin et al., *Proc. Natl. Acad. Sci. USA*, 2007, 104, 16793-97; Laughlin et al., *Science*, 2008, 320, 664-67; Prescher et al., *Nat. Chem. Biol.*, 2005, 1, 13-21; Neef et al, *Angew. Chem. Int. Ed.*, 2009, 48, 1498-500; Ning et al., *Angew. Chem. Int. Ed*, 2008, 47, 2253-55. However, to date, the application of "click" chemistry in living systems, has been largely limited to extracellular targets and no technique has shown reliable ability to specifically label and image intracellular targets. Baskin et al., *QSAR Comb. Sci.*, 2007, 26, 1211-19. There are likely several reasons for this limitation. In addition to fulfilling the stability, toxicity, and chemoselectivity requirements of "click" chemistry, intracellular live cell labeling requires reagents that can easily pass through biological membranes and kinetics that enable rapid labeling even with the low concentrations of agent that make it across the cell membrane. Additionally, a practical intracellular bioorthogonal coupling scheme would need to incorporate a mechanism by which the fluorescent tag increases in fluorescence upon covalent reaction to avoid visualizing accumulated but unreacted imaging probes (i.e., background). This "turn-on" would significantly increase the signal-to-background ratio, which is particularly relevant to imaging targets inside living cells since a stringent washout of unreacted probe is not possible.

In previous years a number of elegant probes have been introduced whose fluorescence increases after azide-alkyne cycloaddition or Staudinger ligation coupling reactions. Hangauer et al., *Angew. Chem. Int. Ed. Engl.*, 2008, 47, 2394-97; Lemieux et al., *J. Am. Chem. Soc.*, 2003, 125, 4708-09; Sivakumar et al., *Org. Lett.*, 2004, 6, 4603-06; Zhou et al., *J. Am. Chem. Soc.*, 2004, 126, 8862-63. Most of these strategies either require a reactive group intimately attached to the fluorophore thus requiring synthesis of new fluorophore scaffolds or take advantage of a FRET based activation requiring appendage of an additional molecule that can act as an energy transfer agent. Furthermore, most probes utilizing these popular coupling schemes have to date been unable to label intracellular targets in live cells.

The bioorthogonal Diels-Alder reaction is compatible with aqueous environments and has second order rate constants that are known to be enhanced up to several hundredfold in aqueous media in comparison to organic solvents.

Graziano, *J. Phys. Org. Chem.*, 2004, 17, 100-01; Rideout et al., *J. Am. Chem. Soc.*, 1980, 102, 7816-17; Seelig et al., *Tetrahedron Lett.*, 1997, 38, 7729-32; Yousaf et al., *J. Am. Chem. Soc.*, 1999, 121, 4286-87. Many Diels-Alder reactions are reversible and therefore may not be suitable for biological labeling. Kwart et al., *Chem. Rev.* 1968, 68, 415-47.

A particularly useful variant of the Diels-Alder reaction employs the inverse electron demand Diels-Alder cycloaddition of olefins with 1,2,4,5-tetrazines results in irreversible coupling giving dihydropyridazine products as shown in Scheme 1.

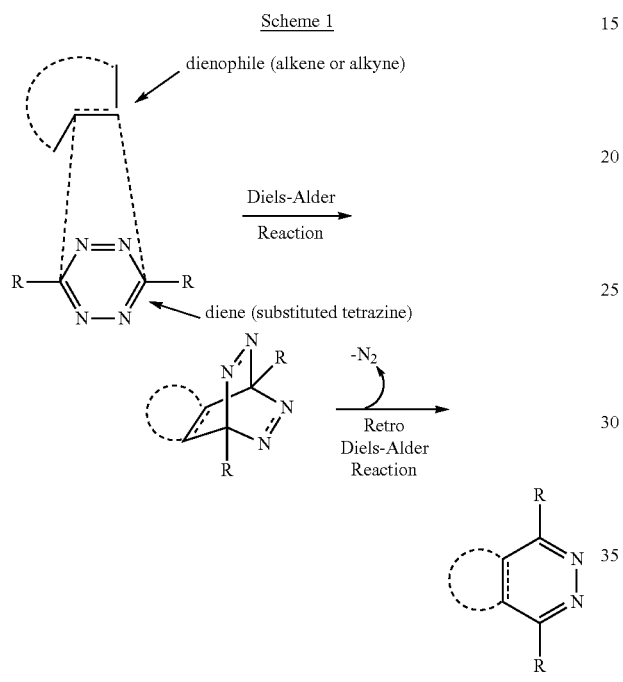

During this reaction, nitrogen is released in a retro Diels-Alder step resulting in an irreversible reaction. Sauer et al., *Chem. Ber.*, 1965, 998, 1435-45. A variety of 1,2,4,5-tetrazines and dienophiles including cyclic and linear alkenes or alkynes have been studied in this reaction. Selection of the appropriate reaction partners, allows for tuning of the coupling rate by several orders of magnitude. The reaction can occur rapidly and at ambient temperatures with a strained alkene or alkynes such as a trans-cyclooctene group or cyclooctyne as a dienophile. Balcar et al., *Tetrahedron Lett.*, 1983, 24, 1481-84; Blackman et al., *J. Am. Chem. Soc.* 2008, 130, 13518-19; Thalhammer et al., *Tetrahedron Lett.*, 1990, 47, 6851-54). See also US 2006/0269942, WO 2007/144200, and US 2008/0181847, US2009/0023916; US2011/0268654 and US2012/0034161.

Application of bioorthogonal coupling technology is described in WO2010/051530. The publication describes materials and methods for delivering a substance specifically to a biological target by applying the inverse electron demand Diels Alder reaction. In general, the method described involves use of a ligand that is specific for a biological target and a substance which is to be brought into proximity with the biological target. The substance can be, e.g., a detectable substance so that the method can be used for diagnostic applications or a therapeutic substance. The ligand and the substance that is to be delivered are brought into proximity by means of a complementary diene (e.g., a 1,2,4,5-tetrazine) attached to one of the components and a dienophile (e.g., a trans-cyclooctene) attached to the second component. The inverse-electron-demand Diels-Alder reaction between the Diels-Alder components, e.g., the 1,2,4,5-tetrazine and a suitable dienophile, e.g., a trans-cyclooctene, serves to bring the components into proximity.

One of the limitations on the broad applicability of the inverse-electron-demand Diels Alder reaction is that relatively few functionalized 1,2,4,5-tetrazines that are suitable for attachment or incorporation into biological molecules, their ligands, or suitable therapeutic or diagnostic molecules are known in the art.

SUMMARY

In one aspect the present disclosure provides a compound of formula (I):

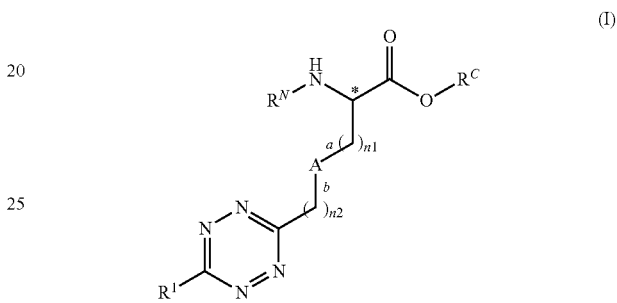

or a salt thereof, wherein the variables and features of the compound are as defined herein.

In a further aspect, the disclosure provides compounds of formula (II):

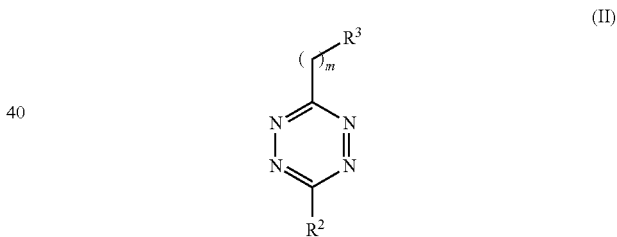

or a salt thereof, wherein the variables and features of the compound are as defined herein.

In another aspect this disclosure provides compounds of formula (III):

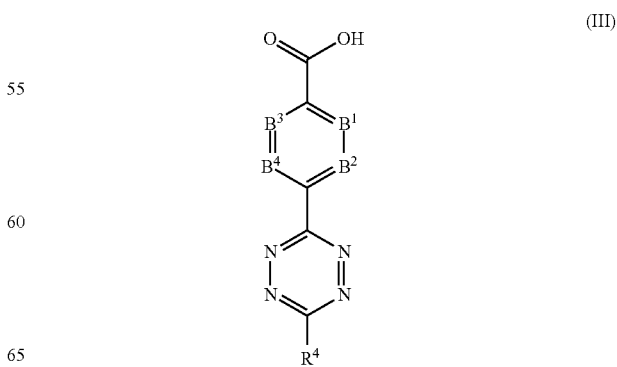

or a salt thereof, wherein the variables and features of the compound are as defined herein.

The compounds described herein are useful as functionalized 1,2,4,5-tetrazine compounds that can be employed for attachment or incorporation into biological molecules, their ligands, or suitable therapeutic or diagnostic molecules. The compounds can be used in bioorthogonal labeling employing inverse-electron-demand Diels Alder reactions of biological molecules, their ligands, and suitable therapeutic or diagnostic molecules with complementary reaction components that incorporate or attach suitable complementary dienophiles, such as trans-cyclooctenes.

The compounds are therefore useful in both diagnostic and therapeutic methods.

BRIEF DESCRIPTION OF THE DRAWING

FIG. 1 shows a scheme for using the bioorthogonal Diels-Alder reaction of a 1,2,4,5-tetrazines for delivering a payload molecule to a biological target.

DETAILED DESCRIPTION

The present disclosure provides new functionalized 1,2,4,5-tetrazine compounds that are useful for attachment or incorporation into biological molecules, their ligands, or suitable therapeutic or diagnostic molecules and for carrying out therapeutic and diagnostic methods employing inverse-electron-demand Diels Alder reactions of such biological molecules, their ligands, and suitable therapeutic or diagnostic molecules with complementary reaction components that incorporate or attach suitable complementary dienophiles, such as trans-cyclooctenes.

In the present description, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

Although methods and materials similar or equivalent to those described herein can be used in the practice or testing of the present invention, suitable methods and materials are described below. In addition, the materials, methods and examples are illustrative only and not intended to be limiting.

I. Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

As used herein, "alkyl" refers to a saturated hydrocarbon chain that may be a straight chain or a branched chain. An alkyl group formally corresponds to an alkane with one C—H bond replaced by the point of attachment of the alkyl group to the remainder of the compound. The term "($C_x$-$C_y$)alkyl" (wherein x and y are integers) by itself or as part of another substituent means, unless otherwise stated, an alkyl group containing from x to y carbon atoms. For example, a ($C_1$-$C_6$)alkyl group may have from one to six (inclusive) carbon atoms in it. Examples of ($C_1$-$C_6$)alkyl groups include, but are not limited to, methyl, ethyl, n-propyl, n-butyl, n-pentyl, n-hexyl, isopropyl, isobutyl, sec-butyl, tert-butyl, isopentyl, neopentyl and isohexyl. The ($C_x$-$C_y$)alkyl groups include ($C_1$-$C_6$)alkyl, ($C_1$-$C_4$)alkyl and ($C_1$-$C_3$)alkyl.

The term "($C_x$-$C_y$)alkylene" (wherein x and y are integers) refers to an alkylene group containing from x to y carbon atoms. An alkylene group formally corresponds to an alkane with two C—H bonds replaced by points of attachment of the alkylene group to the remainder of the compound. Examples are divalent straight hydrocarbon groups consisting of methylene groups, such as, —$CH_2$—, —$CH_2CH_2$—, —$CH_2CH_2CH_2$—. The ($C_x$-$C_y$)alkylene groups include ($C_1$-$C_6$)alkylene and ($C_1$-$C_3$)alkylene.

The term "($C_x$-$C_y$)heteroalkylene" (wherein x and y are integers) refers to a heteroalkylene group containing from x to y carbon atoms. A heteroalkylene group corresponds to an alkylene group wherein one or more of the carbon atoms have been replaced by a heteroatom. The heteroatoms may be independently selected from the group consisting of O, N and S. A divalent heteroatom (e.g., O or S) replaces a methylene group of the alkylene —$CH_2$—, and a trivalent heteroatom (e.g., N) replaces a methine group. Examples are divalent straight hydrocarbon groups consisting of methylene groups, such as, —$CH_2$—, —$CH_2CH_2$—, —$CH_2CH_2CH_2$—. The ($C_x$-$C_y$)alkylene groups include ($C_1$-$C_6$)heteroalkylene and ($C_1$-$C_3$)heteroalkylene.

As used herein, "alkenyl" refers to an unsaturated hydrocarbon chain that includes a C=C double bond. An alkenyl group formally corresponds to an alkene with one C—H bond replaced by the point of attachment of the alkenyl group to the remainder of the compound. The term "($C_x$-$C_y$)alkenyl" (wherein x and y are integers) denotes a radical containing x to y carbons, wherein at least one carbon-carbon double bond is present (therefore x must be at least 2). Some embodiments are 2 to 4 carbons, some embodiments are 2 to 3 carbons and some embodiments have 2 carbons. Alkenyl groups may include both E and Z stereoisomers. An alkenyl group can include more than one double bond. Examples of alkenyl groups include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl, and the like.

As used herein, "alkynyl" refers to an unsaturated hydrocarbon chain that includes a C≡C triple bond. An alkynyl group formally corresponds to an alkyne with one C—H bond replaced by the point of attachment of the alkyl group to the remainder of the compound. The term "($C_x$-$C_y$)alkynyl" (wherein x and y are integers) denotes a radical containing x to y carbons, wherein at least one carbon-carbon triple bond is present (therefore x must be at least 2). Some embodiments are 2 to 4 carbons, some embodiments are 2 to 3 carbons and some embodiments have 2 carbons. Examples of an alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

As used herein, "halo" or "halogen" refers to —F, —Cl, —Br and —I.

The term "haloalkyl" as used herein refers to an alkyl group in which one or more of the hydrogen atoms has been replaced by a halogen atom. The term "$(C_x-C_y)$haloalkyl" (wherein x and y are integers) by itself or as part of another substituent means, unless otherwise stated, an alkyl group containing from x to y carbon atoms. The alkyl may be substituted with one halogen up to fully substituted, e.g., as represented by the formula $C_nF_{2n+1}$; when more than one halogen is present they may be the same or different and selected from F, Cl, Br or I. Some embodiments are 1 to 3 carbons. Haloalkyl groups may be straight-chained or branched. Examples include fluoromethyl, difluoromethyl, trifluoromethyl, chlorodifluoromethyl, 2,2,2-trifluoroethyl, pentafluoroethyl and the like. The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "aromatic" refers to a carbocycle or heterocycle having one or more polyunsaturated rings having aromatic character (i.e., having (4n+2) delocalized π (pi) electrons where n is an integer).

As used herein, "aryl," employed alone or in combination with other terms, refers to an aromatic hydrocarbon group. The aryl group may be composed of, e.g., monocyclic or bicyclic rings and may contain, e.g., from 6 to 12 carbons in the ring, such as phenyl, biphenyl and naphthyl. The term "$(C_x-C_y)$aryl" (wherein x and y are integers) denotes an aryl group containing from x to y ring carbon atoms. Examples of a $(C_6-C_{14})$aryl group include, but are not limited to, phenyl, α-naphthyl, β-naphthyl, biphenyl, anthryl, tetrahydronaphthyl, fluorenyl, indanyl, biphenylenyl and acenanaphthyl. Examples of a $C_6-C_{10}$ aryl group include, but are not limited to, phenyl, α-naphthyl, β-naphthyl, biphenyl and tetrahydronaphthyl.

An aryl group can be unsubstituted or substituted. A substituted aryl group can be substituted with one or more groups, e.g., 1, 2 or 3 groups, including: $(C_1-C_6)$alkyl, $(C_2-C_6)$alkenyl, $(C_2-C_6)$alkynyl, halogen, $(C_1-C_6)$haloalkyl, —CN, —$NO_2$, —C(=O)R, —C(=O)OR, —C(=O)$NR_2$, —C(=NR)$NR_2$, —$NR_2$, —NRC(=O)R, —NRC(=O)O$(C_1-C_6)$alkyl, —NRC(=O)$NR_2$, —NRC(=NR)$NR_2$, —$NRSO_2R$, —OR, —O$(C_1-C_6)$haloalkyl, —OC(=O)R, —OC(=O)O$(C_1-C_6)$alkyl, —OC(=O)$NR_2$, —SR, —S(O)R, —$SO_2R$, —$OSO_2(C_1-C_6)$alkyl, —$SO_2NR_2$, —$(C_1-C_6)$alkylene-CN, —$(C_1-C_6)$alkylene-C(=O)OR, —$(C_1-C_6)$alkylene-C(=O)$NR_2$, —$(C_1-C_6)$alkylene-OR, —$(C_1-C_6)$alkylene-OC(=O)R, —$(C_1-C_6)$alkylene-$NR_2$, —$(C_1-C_6)$alkylene-NRC(=O)R, —NR$(C_1-C_6)$alkylene-C(=O)OR, —NR$(C_1-C_6)$alkylene-C(=O)$NR_2$, —NR$(C_2-C_6)$alkylene-OR, —NR$(C_2-C_6)$alkylene-OC(=O)R, —NR$(C_2-C_6)$alkylene-$NR_2$, —NR$(C_2-C_6)$alkylene-NRC(=O)R, —O$(C_1-C_6)$alkylene-C(=O)OR, —O$(C_1-C_6)$alkylene-C(=O)$NR_2$, —O$(C_2-C_6)$alkylene-OR, —O$(C_2-C_6)$alkylene-OC(=O)R, —O$(C_2-C_6)$alkylene-$NR_2$ and —O$(C_2-C_6)$alkylene-NRC(=O)R, wherein each R group is hydrogen or $(C_1-C_6$ alkyl).

The term "heteroaryl" or "heteroaromatic" as used herein refers to an aromatic ring system having at least one heteroatom in at least one ring, and from 2 to 9 carbon atoms in the ring system. The heteroaryl group has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaryls include furyl, thienyl, pyridyl, oxazolyl, pyrrolyl, indolyl, quinolinyl or isoquinolinyl, and the like. The heteroatoms of the heteroaryl ring system can include heteroatoms selected from one or more of nitrogen, oxygen and sulfur.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1, 5-naphthyridinyl, 1, 8-naphthyridinyl, 1,4-benzodioxanyl, coumarin, dihydrocoumarin, benzofuryl, particularly 3-, 4-, 5-, 6- and 7-benzofuryl, 2, 3-dihydrobenzofuryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl and benztriazolyl.

A heteroaryl group can be unsubstituted or substituted. A substituted heteroaryl group can be substituted with one or more groups, e.g., 1, 2 or 3 groups, including: $(C_1-C_6)$alkyl, $(C_2-C_6)$alkenyl, $(C_2-C_6)$alkynyl, halogen, $(C_1-C_6)$haloalkyl, —CN, —$NO_2$, —C(=O)R, —C(=O)OR, —C(=O)$NR_2$, —C(=NR)$NR_2$, —$NR_2$, —NRC(=O)R, —NRC(=O)O$(C_1-C_6)$alkyl, —NRC(=O)$NR_2$, —NRC(=NR)$NR_2$, —$NRSO_2R$, —OR, —O$(C_1-C_6)$haloalkyl, —OC(=O)R, —OC(=O)O$(C_1-C_6)$alkyl, —OC(=O)$NR_2$, —SR, —S(O)R, —$SO_2R$, —$OSO_2(C_1-C_6)$alkyl, —$SO_2NR_2$, —$(C_1-C_6)$alkylene-CN, —$(C_1-C_6)$alkylene-C(=O)OR, —$(C_1-C_6)$alkylene-C(=O)$NR_2$, —$(C_1-C_6)$alkylene-OR, —$(C_1-C_6)$alkylene-OC(=O)R, —$(C_1-C_6)$alkylene-$NR_2$, —$(C_1-C_6)$alkylene-NRC(=O)R, —NR$(C_1-C_6)$alkylene-C(=O)OR, —NR$(C_1-C_6)$alkylene-C(=O)$NR_2$, —NR$(C_2-C_6)$alkylene-OR, —NR$(C_2-C_6)$alkylene-OC(=O)R, —NR$(C_2-C_6)$alkylene-$NR_2$, —NR$(C_2-C_6)$alkylene-NRC(=O)R, —O$(C_1-C_6)$alkylene-C(=O)OR, —O$(C_1-C_6)$alkylene-C(=O)$NR_2$, —O$(C_2-C_6)$alkylene-OR, —O$(C_2-C_6)$alkylene-OC(=O)R, —O$(C_2-C_6)$alkylene-$NR_2$ and —O$(C_2-C_6)$alkylene-NRC(=O)R, wherein each R group is hydrogen or $(C_1-C_6$ alkyl).

The aforementioned listing of heteroaryl moieties is intended to be representative and not limiting.

The term "protecting group" refers to a chemical functional group that can be used to derivatize a reactive functional group present in a molecule to prevent undesired reactions from occurring under particular sets of reaction conditions but which is capable of being introduced and removed selectively under known reaction conditions. The chemistry and use of functional groups is familiar to one skilled in the art. Discussion of protecting groups can be found, e.g., in *Protecting Group Chemistry*, 1st Ed., Oxford University Press, 2000; *March's Advanced Organic chemistry: Reactions, Mechanisms, and Structure*, 5th Ed., Wiley- Interscience Publication, 2001; Peturssion, S. et al., "*Protecting Groups in Carbohydrate Chemistry*," *J. Chem. Educ.*, 1997, 74(11), 1297, Wuts et al., *Protective Groups in Organic Synthesis*, 4$^{th}$ Ed., Wiley Interscience (2007).

The term "substituted" means that an atom or group of atoms formally replaces hydrogen as a "substituent" attached to another group. The term "substituted", unless otherwise indicated, refers to any level of substitution, namely mono-, di-, tri-, tetra- or penta-substitution, where such substitution is permitted. The substituents are independently selected, and substitution may be at any chemically accessible position. When groups are described herein as being substituted, the substituents can include, but are not limited to, $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —OC(=O)Ar, —C(=O)OR, —C(=O)NR$_2$, —C(=NR)NR$_2$, —OR, —Ar, —OAr, —(($C_1$-$C_6$)alkylene)Ar, —O(($C_1$-$C_6$)alkylene)Ar, —OC(=O)($C_1$-$C_6$)alkyl, —OC(=O)O($C_1$-$C_6$)alkyl, —OC(=O)NR$_2$, —NR$_2$, —NRAr, —NR(($C_1$-$C_6$)alkylene)Ar, —NRC(=O)R, —NRC(=O)Ar, —NRC(=O)O($C_1$-$C_6$)alkyl, —NRC(=O)NR$_2$, —NRSO$_2$R, —SR, —S(O)R, —SO$_2$R, —OSO$_2$($C_1$-$C_6$)alkyl, —SO$_2$NR$_2$, $(C_1-C_8)$perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$, wherein each R group is hydrogen or ($C_1$-$C_6$ alkyl), e.g., methyl and wherein each Ar is independently unsubstituted aryl or heteroaryl or aryl or heteroaryl substituted with one or more of $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —OR, —OC(=O)($C_1$-$C_6$)alkyl, —OC(=O)O($C_1$-$C_6$)alkyl, —OC(=O)NR$_2$, —NR$_2$, —NRC(=O)R, —NRC(=O)O($C_1$-$C_6$)alkyl, —NRC(=O)NR$_2$, —NRSO$_2$R, —SR, —S(O)R, —SO$_2$R, —OSO$_2$($C_1$-$C_6$)alkyl, —SO$_2$NR$_2$, $(C_1-C_8)$perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$ wherein each R group is hydrogen or ($C_1$-$C_6$ alkyl).

The term "salt" includes any ionic form of a compound and one or more counterionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzenesulfonate, p-toluenesulfonate, p-trifluoromethylbenzenesulfonate, hydroxide, aluminates and borates. Exemplary cations include, but are not limited to, monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as nonmetal cations, such as ammonium salts.

References to the compounds described and disclosed herein are considered to include both the free base and all addition salts. The addition salts may be either salts with pharmaceutically acceptable cations such as Na$^+$, Ca$^{2+}$, K$^+$ or Na$^+$ at a terminal acid group, such as when the C-terminal amino acid is Gly or OH is present, or with a pharmaceutically acceptable acid addition salt at a basic center of the peptide, such as in an Arg unit. The acetate salt forms are useful, and hydrochloride, hydrobromide and salts with other strong acids are also useful. In the isolation procedures outlined in the Examples, the peptide product is often isolated and purified as an acetate salt. The compounds may also form inner salts or zwitterions when a free terminal carboxy group is present. The term "pharmaceutically acceptable salt" refers to salts which possess toxicity profiles within a range that affords utility in pharmaceutical applications. Pharmaceutically unacceptable salts may nonetheless possess properties such as high crystallinity, which may render them useful, e.g., in processes of synthesis, purification or formulation of compounds described herein. In general the useful properties of the compounds described herein do not depend on whether the compound is or is not in a salt form, so unless clearly indicated otherwise (such as specifying that the compound should be in "free base" or "free acid" form), reference in the specification to a compound should be understood as including salt forms of the compound, whether or not this is explicitly stated. Preparation and selection of suitable salt forms is described in Stahl et al., *Handbook of Pharmaceutical Salts: Properties, Selection, and Use*, Wiley-VCH 2002.

When in the solid state, the compounds described herein and salts thereof may occur in various forms and may, e.g., take the form of solvates, including hydrates. In general, the useful properties of the compounds described herein do not depend on whether the compound or salt thereof is or is in a particular solid state form, such as a polymorph or solvate, so unless clearly indicated otherwise reference in the specification to compounds and salts should be understood as encompassing any solid state form of the compound, whether or not this is explicitly stated.

Compounds provided herein can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Selectively binds to" or "selectively reacts with" means that one molecule, such as a targeting ligand preferentially binds to or reacts with another molecule, such as a target molecule, e.g., a nucleic acid or a protein, in the presence of other molecules in a sample.

The following abbreviations may also be found herein: AcOH (acetic acid); BOC (tert-butoxycarbonyl); CHCl$_3$ (chloroform); CuSO$_4$ (copper sulfate); DCM (dichloromethane); DIAD (N,N'-diisopropyl azidodicarboxylate); DIC (N,N'-diisopropylcarbodiimide); DIPEA (N,N'-diisopropylethylamine; DME (1,2-dimethoxyethane); DMF (N,N'-dimethylformamide); Et (ethyl); EtOAc (ethyl acetate); eq. (equivalent(s)); FMOC (9-fluorenylmethylmethoxycarbonyl); h (hour(s)); ivDde (1-(4,4-dimethyl-2,6-dioxocyclohex-1-ylidene)3-methylbutyl; HIPF (1,1,1,3,3,3-hexafluoro-2-propanol; HOBt (N-hydroxybenzotriazole); HPLC (high-performance liquid chromatography); LC (liquid chromatography); MeOH (methanol); MgSO$_4$ (magnesium sulfate); min. (minute(s)); MS (mass spectrometry); Mtt (4-methyltrityl); NaHCO$_3$(sodium bicarbonate); NaOH (sodium hydroxide); Na₂SO₃ (sodium sulfite); NH₄Cl (ammonium chloride); NMM (4-methylmorpholine); NMO (N-methyolmorpholine-N-oxide); Pbf (2,2,4,6,7-pentamethyldihydrobenzofuran-5-sulfonyl); t-Bu (tert-butyl); TCO (trans-cyclooctene); TEAP (triethylammonium phosphate); TFA (trifluroracetic acid); TFE (2,2,2-trifluoroethanol); THF (tetrahydrofuran); TMSOTf (trimethylsilyl trifluoromethanesulfonate); TIS (triisopropylsilane); TPAP (tetrapropylammonium perrhuthenate); TPP (triphenylphosphine); and Trt (trityl [triphenylmethyl, (C₆H₅)₃C—]); Tz (1,2,4,5-tetrazine).

II. Novel Compounds

A. Compounds of Formula (I)

This disclosure provides a compound of formula (I):

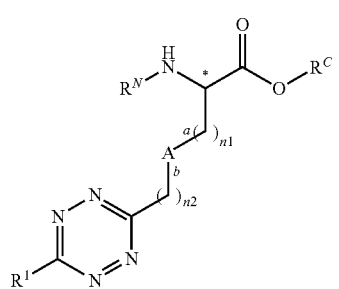

(I)

or a salt thereof, wherein:

$R^N$ is hydrogen or an amine protecting group;

$R^C$ is hydrogen or a carboxyl protecting group;

$R^1$ is hydrogen or $(C_1-C_6)$alkyl or substituted $(C_1-C_6)$alkyl;

A is absent or is a group selected from groups of formulae (A1), (A2), (A3), (A4) and (A5):

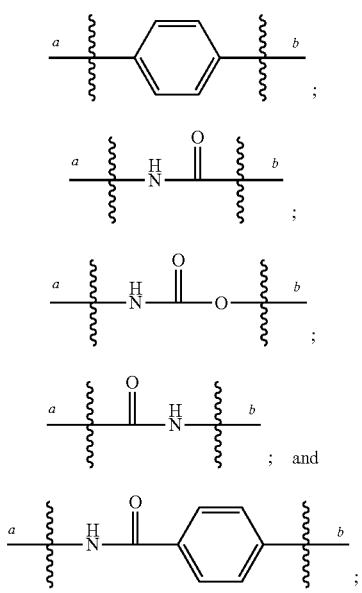

n1 is 1, 2, 3, 4, 5 or 6;

n2 is 0, 1, 2, 3, 4, 5 or 6;

a and b denote bonds attaching A to the remainder of the molecule or together form a single bond when A is absent.

In some embodiments of the compounds of formula (I), $R^N$ is hydrogen.

In some embodiments of the compounds of formula (I), $R^N$ is an amine protecting group. The amine protecting groups that can be used include any of those discussed in Chapter 7 (pp. 696-926) of Wuts et al., *Protective Groups in Organic Synthesis*, Wiley Interscience 2007, and include: methyl carbamate, ethyl carbamante, 9-fluorenylmethyl carbamate (FMOC), 9-(2-sulfo)fluorenylmethyl carbamate, 9-(2,7-dibromo)fluoroenylmethyl carbamate, 2,7-di-tert-butyl-[9-(10,10-dioxo-10,10,10,10-tetrahydrothioxanthyl)] methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-tert-butylphenyl)-1-methylethyl carbamate (t-Bumeoc), 2-(2'- and 4'-pyridyl)ethyl carbamate (Pyoc), 2-(N,N'-dicyclohexylcarboxamido)ethyl carbamate, tert-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N-p-toluenesulfonylaminocarbonyl derivative, IV-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N'-dimethylcarboxamido)benzyl carbamate, 1,1-dimethyl-3-(N,N'-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-tert-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In some embodiments of the compounds of formula (I), $R^N$ is a tert-butyloxycarbonyl group.

In some embodiments of the compounds of formula (I), $R^N$ is a 9-fluorenylmethoxycarbonyl group.

In some embodiments of the compounds of formula (I), $R^C$ is hydrogen.

In some embodiments of the compounds of formula (I), $R^C$ is a carboxyl protecting group. The amine protecting groups that can be used include any of those discussed in Chapter 5 (pp. 533-646) of Wuts et al., *Protective Groups in Organic Synthesis*, Wiley Interscience 2007, and include: methyl, ethyl, 2-N-(morpholino)ethyl, choline, methoxyethyl, 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl-α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl) ethyl, 2-(p-methoxyphenyl)ethyl, 2-(diphenylphosphino) ethyl, 1-methyl-1-phenylethyl, 2-(4-acetyl-2-nitrophenyl) ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{N-[1-(4,4-dimethyl-2,6-dioxocyclohexylidene)-3-methylbutyl]amino}benzy-1, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl.

In some embodiments of the compounds of formula (I), $R^C$ is $(C_1-C_6)$alkyl, e.g., methyl or ethyl.

In some embodiments of the compounds of formula (I), $R^1$ is hydrogen.

In some embodiments of the compounds of formula (I), $R^1$ is $(C_1-C_6)$alkyl, e.g., methyl or ethyl.

In some embodiments of the compounds of formula (I), $R^1$ is substituted $(C_1-C_6)$alkyl. The substituted $(C_1-C_6)$alkyl can be substituted, e.g., by 1, 2, 3, 4, or 5 substituents selected from $(C_2-C_6)$alkenyl, $(C_2-C_6)$alkynyl, halogen, $(C_1-C_6)$haloalkyl, —CN, —NO₂, —C(=O)R, —OC(=O)Ar, —C(=O)OR, —C(=O)NR₂, —C(=NR)NR₂, —OR, Ar, —OAr, —((C₁-C₆)alkylene)Ar, —O((C₁-C₆)alkylene)Ar, —OC(=O)(C₁-C₆)alkyl, —OC(=O)O(C₁-C₆)alkyl, —OC(=O)NR₂, —NR₂, —NRAr, —NR((C₁-C₆)alkylene)Ar, —NRC(=O)R, —NRC(=O)Ar, —NRC(=O)O(C₁-C₆)alkyl, —NRC(=O)NR₂, —NRSO₂R, —SR, —S(O)R, —SO₂R, —OSO₂(C₁-C₆)alkyl, —SO₂NR₂, —(C₁-C₈)perfluoroalkyl, —(C₂-C₆)alkylene-OR, —O(C₂-C₆)alkylene-N ((C₁-C₆)alkyl)₂, —P(=O)(OR)₂, and —OP(=O)(OR)₂, wherein each R group is hydrogen or $(C_1-C_6$ alkyl), e.g., methyl and wherein each Ar is independently unsubstituted aryl or heteroaryl or aryl or heteroaryl substituted with one or more of $(C_1-C_6)$alkyl, $(C_2-C_6)$alkenyl, $(C_2-C_6)$alkynyl, halogen, $(C_1-C_6)$haloalkyl, —CN, —NO₂, —C(=O)R, —C(=O)OR, —C(=O)NR₂, —C(=NR)NR₂, —OR, —OC(=O)(C₁-C₆)alkyl, —OC(=O)O(C₁-C₆)alkyl, —OC(=O)NR₂, —NR₂, —NRC(=O)R, —NRC(=O)O(C₁-C₆) alkyl, —NRC(=O)NR₂, —NRSO₂R, —SR, —S(O)R, —SO₂R, —OSO₂(C₁-C₆)alkyl, —SO₂NR₂, (C₁-C₈)perfluoroalkyl, —(C₂-C₆)alkylene-OR, —O(C₂-C₆)alkylene-N ((C₁-C₆)alkyl)₂, —P(=O)(OR)₂, —OP(=O)(OR)₂ wherein each R group is hydrogen or ($C_1$-$C_6$ alkyl). In some embodiments, the substituted ($C_1$-$C_6$)alkyl can be, e.g., substituted ($C_1$-$C_6$)haloalkyl.

In some embodiments of the compounds of formula (I), n1 is 1.

In some embodiments of the compounds of formula (I), n1 is 2.

In some embodiments of the compounds of formula (I), n1 is 3.

In some embodiments of the compounds of formula (I), n1 is 4.

In some embodiments of the compounds of formula (I), n1 is 5.

In some embodiments of the compounds of formula (I), n2 is 0.

In some embodiments of the compounds of formula (I), n2 is 1.

In some embodiments of the compounds of formula (I), n2 is 2.

In some embodiments of the compounds of formula (I), n2 is 3.

In some embodiments of the compounds of formula (I), n2 is 4.

In some embodiments of the compounds of formula (I), n2 is 5.

In some embodiments of the compounds of formula (I), A is absent.

In some embodiments of the compounds of formula (I), A is absent and n2 is 0 and the compound is according to the formula (IA):

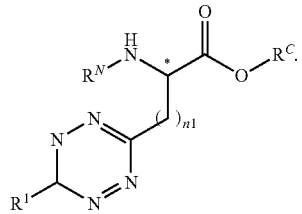

(IA)

In some embodiments of the compounds of formula (IA), n1 is 1.

Particular compounds according to formula (IA) include compounds of the following formulae:

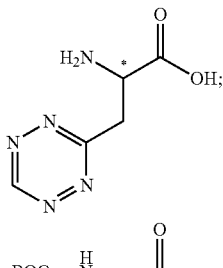 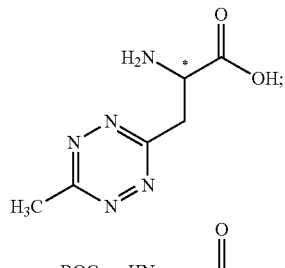

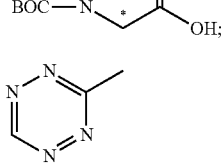

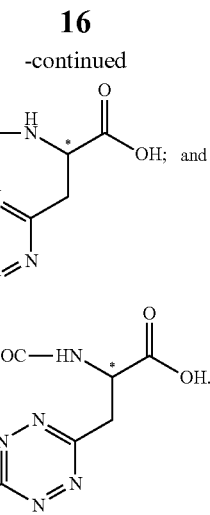

In some embodiments of the compounds of formula (I), A is according to formula (A1):

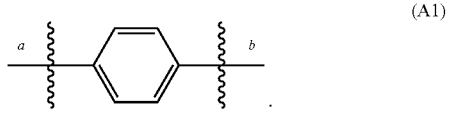

(A1)

In some embodiments of the compounds of formula (I), A is according to formula (A1) and n2 is 0 and the compound is according to the formula (IB):

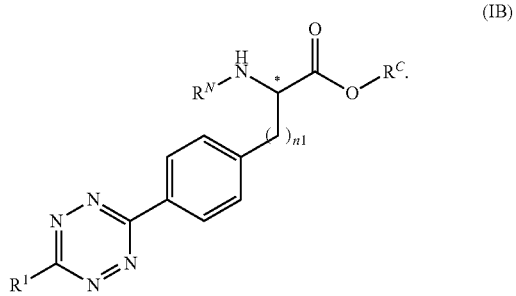

(IB)

Particular compounds according to formula (IB) include compounds of the following formulae:

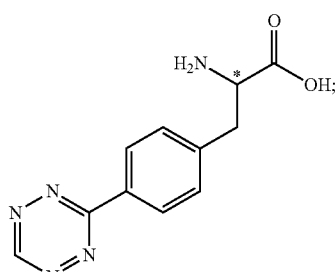

-continued

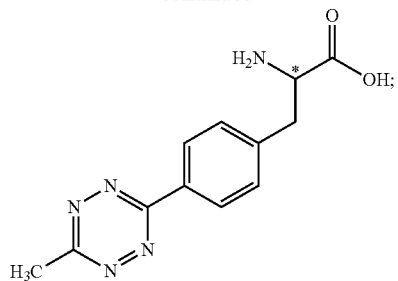

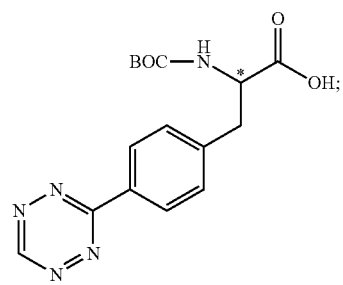

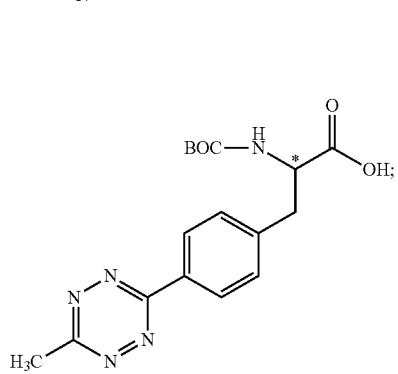

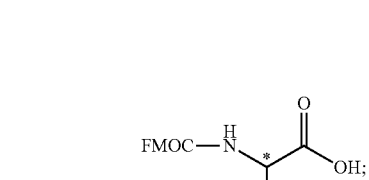

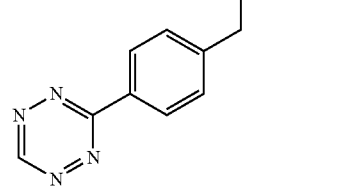

In some embodiments of the compounds of formula (I), A is according to formula (A2):

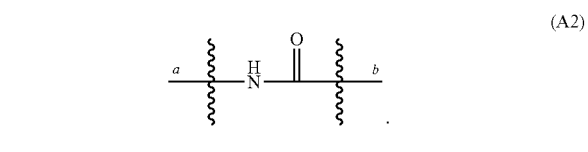
(A2)

In some embodiments of the compounds of formula (I), A is according to formula (A2) and n1 is 3, 4 or 5.

In some embodiments of the compounds of formula (I), A is according to formula (A2) and the compound is according to the formula (IC):

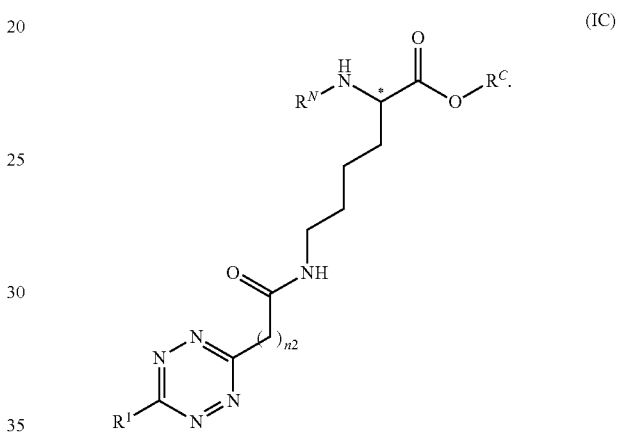
(IC)

In some embodiments of the compounds of formula (IC), n2 is 0, 1, or 2.

In some embodiments of the compounds of formula (IC), n2 is 2.

Particular compounds according to formula (I) wherein A is (A2) include the compounds of the following formulae:

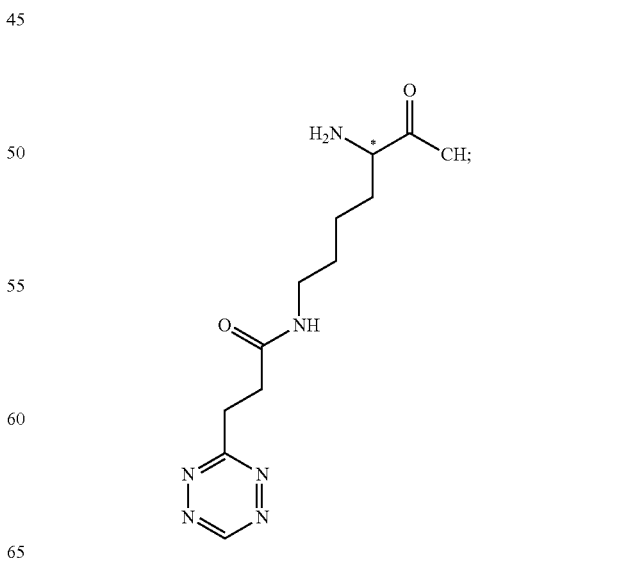

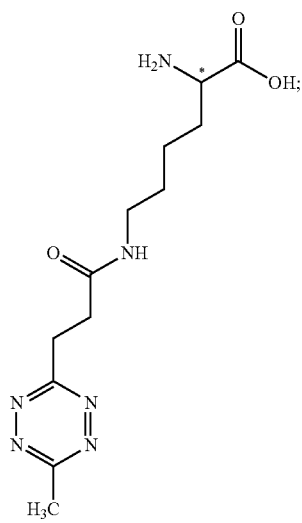
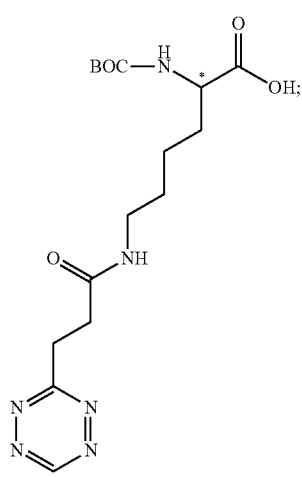
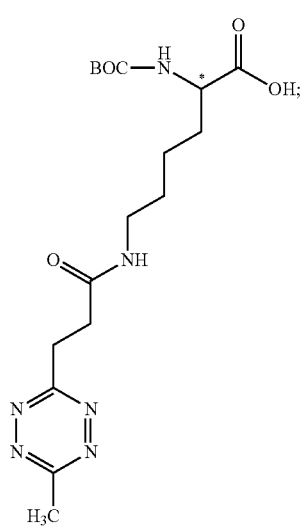
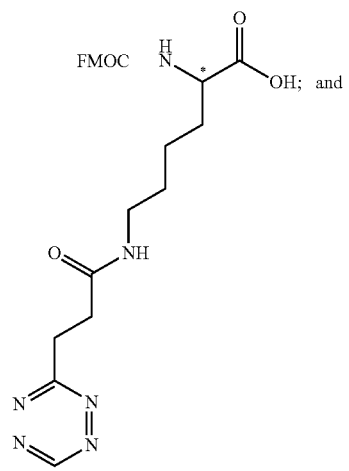
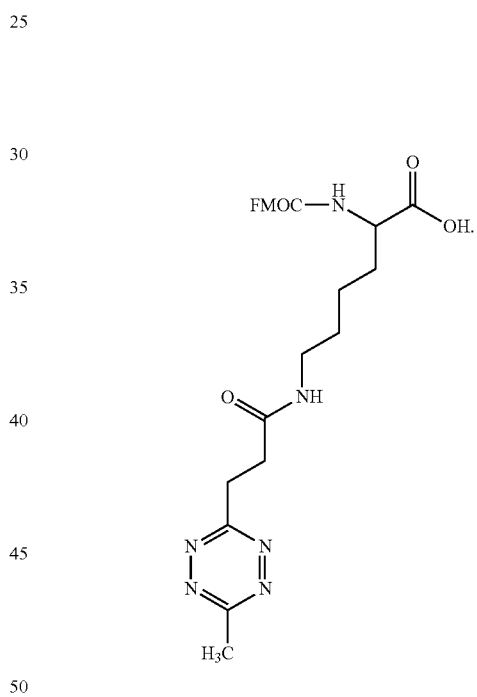
In some embodiments of the compounds of formula (I), A is according to formula (A3):
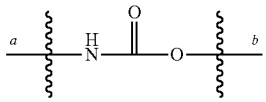
(A3)
In some embodiments of the compounds of formula (I), A is according to formula (A3), n2 is other than 0.
In some embodiments of the compounds of formula (I), A is according to formula (A3), n1 is 4 and the compound is according to the formula (ID):

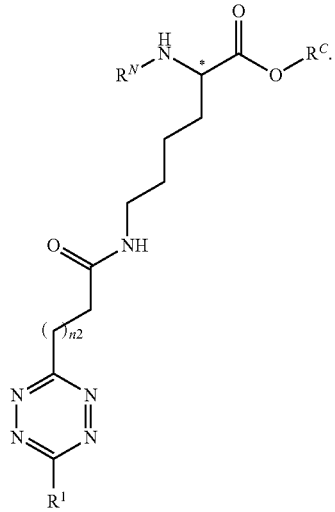
(ID)
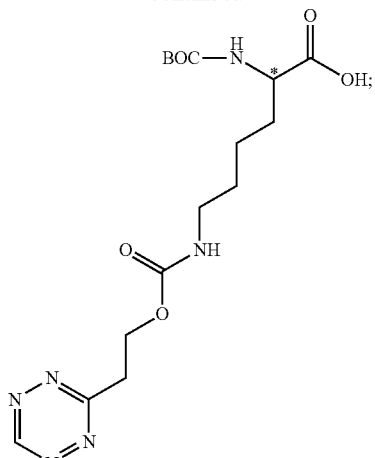
Particular compounds according to formula (ID) include compounds of the following formulae:
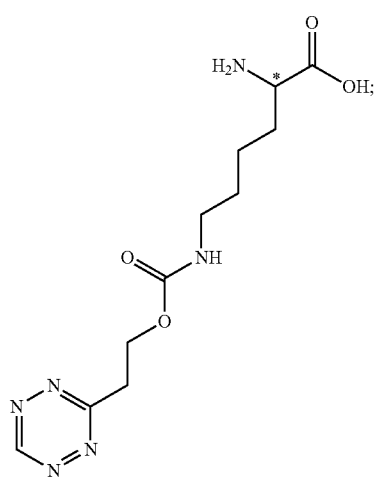
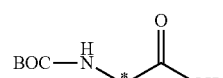
-continued
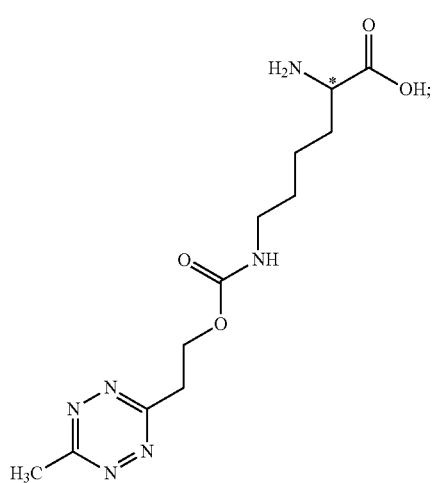
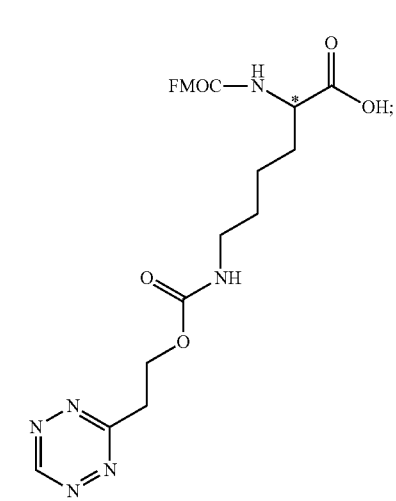

-continued

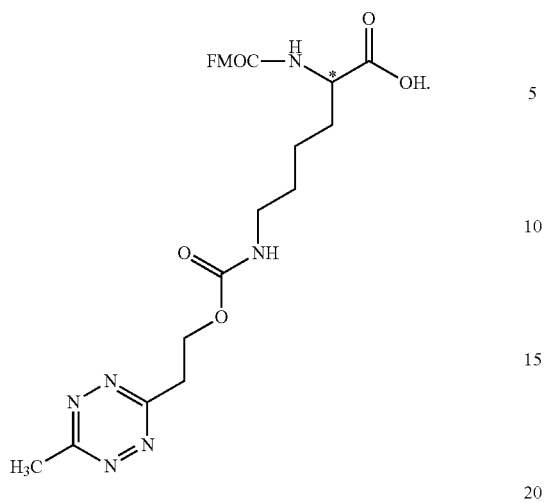

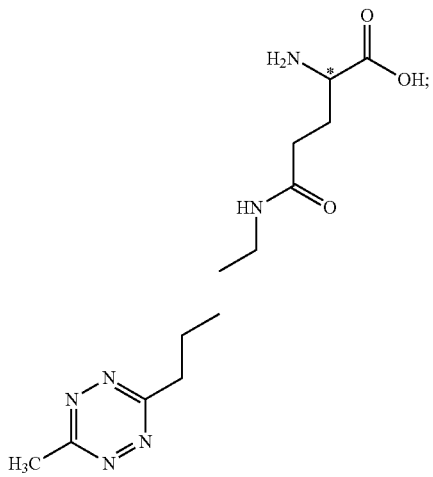

In some embodiments of the compounds of formula (I), A is according to formula (A4):

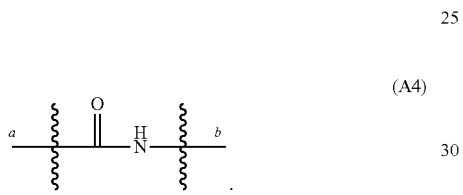

(A4)

In some embodiments of the compounds of formula (I) wherein A is according to formula (A4), n1 is 1.

In some embodiments of the compounds of formula (I) wherein A is according to formula (A4), n1 is 2.

In some embodiments of the compounds of formula (I) wherein A is according to formula (A4), n2 is 5.

Particular compounds according to formula (I) wherein A is according to formula (A4) include compounds according to the following formulae:

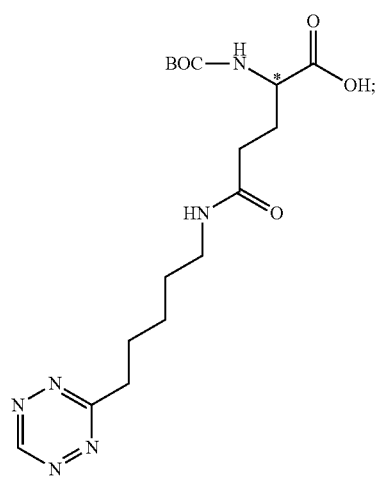

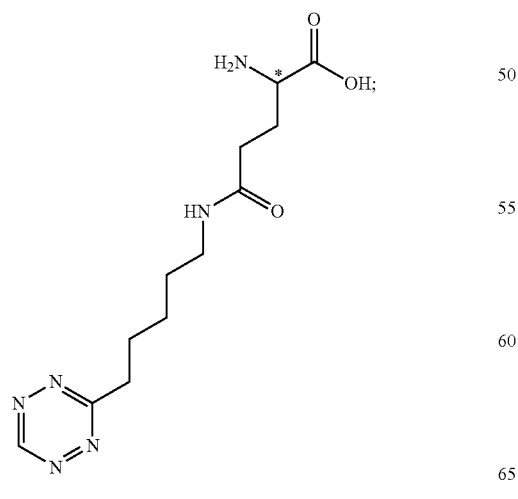

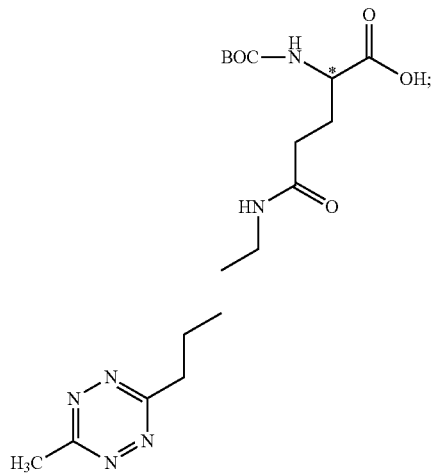

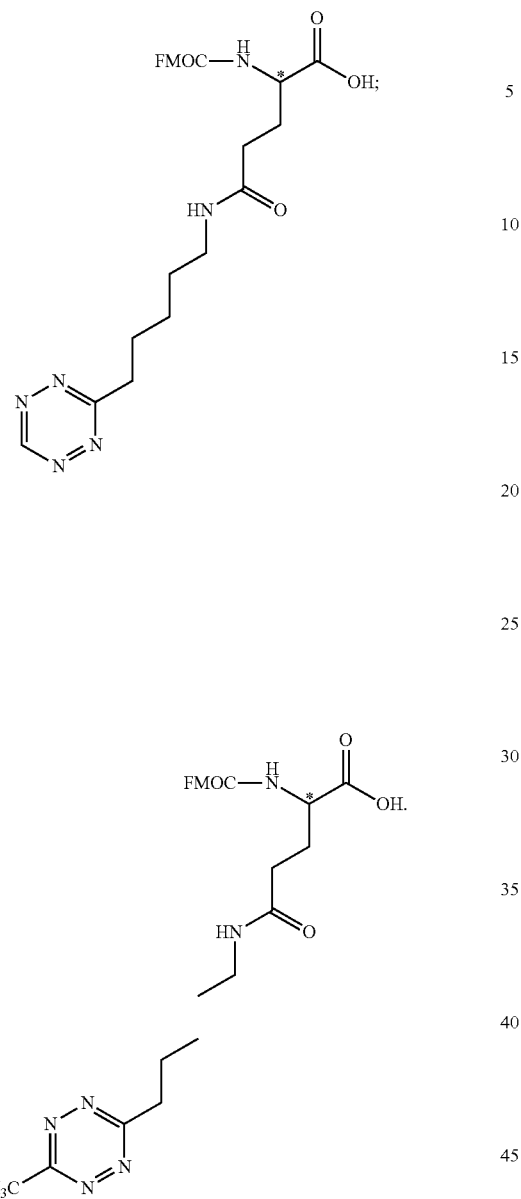

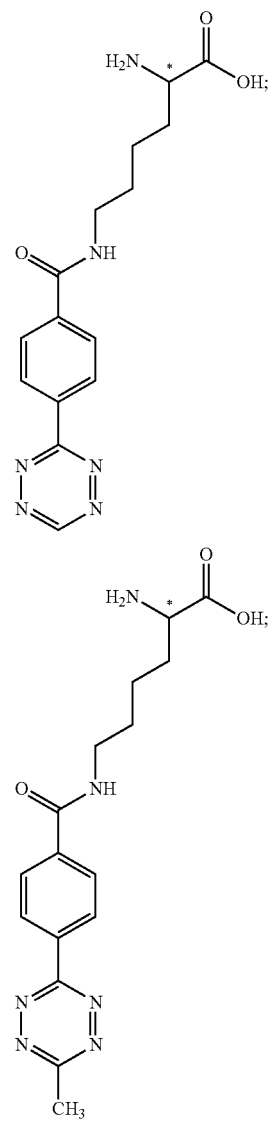

In some embodiments of the compounds of formula (I), A is according to formula (A5):

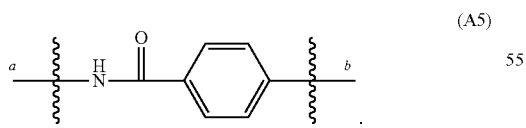

(A5)

In some embodiments of the compounds of formula (I), A is according to formula (A5), n1 is 4.

In some embodiments of the compounds of formula (I), A is according to formula (A5), n2 is 0.

Particular compounds according to formula (I) wherein A is according to formula (A5) include compounds according to the following formulae:

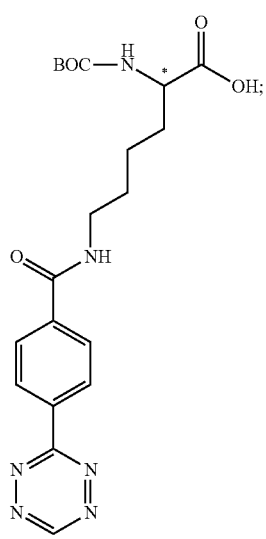

-continued

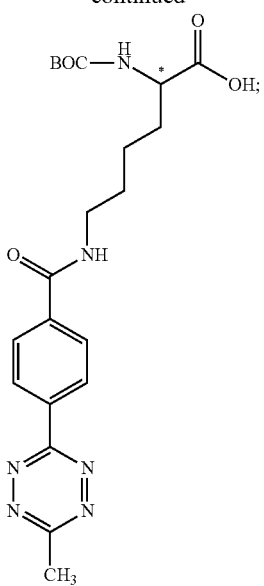

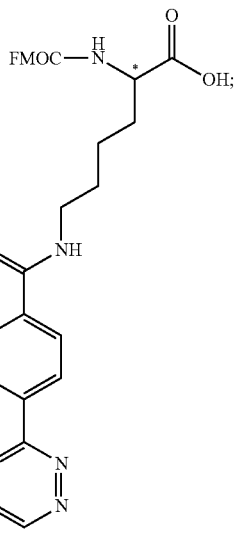

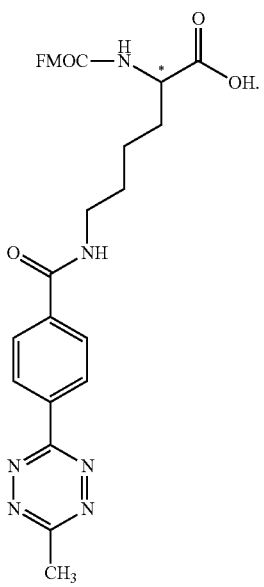

In any of the amino acids compounds of formula (I) described herein, the amino acid may be racemic.

In any of the amino acids compounds of formula (I) described herein, the amino acid may have (L) configuration.

In any of the amino acids compounds of formula (I) described herein, the amino acid may have (D) configuration.

B. Compounds of Formula (II)

This disclosure provides compounds of formula (II):

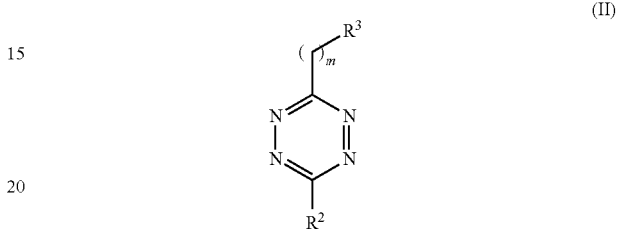

(II)

or a salt thereof, wherein:
$R^2$ is hydrogen, $(C_1-C_6)$alkyl or substituted $(C_1-C_6)$alkyl;
$R^3$ is selected from —$CO_2H$, $OSO_2(C_1-C_6)$alkyl, $OSO_2Ar$,

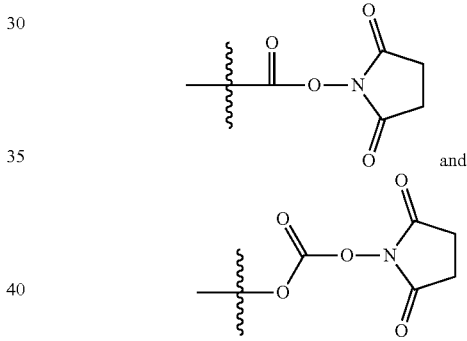

and

Ar is aryl or substituted aryl; and
m is selected from 1, 2, 3, 4, or 5.

In some embodiments of the compounds of formula (II), $R^2$ is hydrogen.

In some embodiments of the compounds of formula (II), $R^2$ is $(C_1-C_6)$alkyl.

In some embodiments of the compounds of formula (II), $R^2$ is methyl.

In some embodiments of the compounds of formula (II), $R^2$ is substituted $(C_1-C_6)$alkyl. The substituted $(C_1-C_6)$alkyl can be substituted, e.g., by 1, 2, 3, 4, or 5 substituents selected from $(C_2-C_6)$alkenyl, $(C_2-C_6)$alkynyl, halogen, $(C_1-C_6)$haloalkyl, —CN, —$NO_2$, —C(=O)R, —OC(=O)Ar, —C(=O)OR, —C(=O)$NR_2$, —C(=NR)$NR_2$, —OR, Ar, —OAr, —(($C_1-C_6$)alkylene)Ar, —O(($C_1-C_6$)alkylene)Ar, —OC(=O)($C_1-C_6$)alkyl, —OC(=O)O($C_1-C_6$)alkyl, —OC(=O)$NR_2$, —$NR_2$, —NRAr, —NR(($C_1-C_6$)alkylene)Ar, —NRC(=O)R, —NRC(=O)Ar, —NRC(=O)O($C_1-C_6$)alkyl, —NRC(=O)$NR_2$, —$NRSO_2R$, —SR, —S(O)R, —$SO_2R$, —$OSO_2(C_1-C_6)$alkyl, —$SO_2NR_2$, —$(C_1-C_8)$perfluoroalkyl, —$(C_2-C_6)$alkylene-OR, —O$(C_2-C_6)$alkylene-N(($C_1-C_6$)alkyl)$_2$, —P(=O)(OR)$_2$, and —OP(=O)(OR)$_2$, wherein each R group is hydrogen or $(C_1-C_6$ alkyl), e.g., methyl and wherein each Ar is independently unsubstituted aryl or heteroaryl or aryl or heteroaryl substituted with one or more of $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —OR, —OC(=O)($C_1-C_6$)alkyl, —OC(=O)O($C_1-C_6$)alkyl, —OC(=O)NR$_2$, —NR$_2$, —NRC(=O)R, —NRC(=O)O($C_1-C_6$)alkyl, —NRC(=O)NR$_2$, —NRSO$_2$R, —SR, —S(O)R, —SO$_2$R, —OSO$_2$($C_1-C_6$)alkyl, —SO$_2$NR$_2$, $(C_1-C_8)$perfluoroalkyl, —($C_2-C_6$)alkylene-OR, —O($C_2-C_6$)alkylene-N(($C_1-C_6$)alkyl)$_2$, —P(=O)(OR)$_2$, —OP(=O)(OR)$_2$ wherein each R group is hydrogen or $(C_1-C_6$ alkyl). In some embodiments, the substituted $(C_1-C_6)$alkyl can be, e.g., substituted $(C_1-C_6)$haloalkyl.

In some embodiments of the compounds of formula (II), m is 2.

In some embodiments of the compounds of formula (II), $R^3$ is selected from:

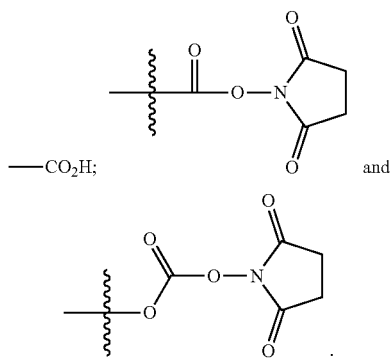

In some embodiments of the compounds of formula (II), $R^3$ is fluorine.

In some embodiments of the compounds of formula (II), $R^3$ is OSO$_2$Ar.

In some embodiments of the compounds of formula (II), $R^3$ is OSO$_2$p-Tolyl.

Particular compounds according to formula (II) include compounds of the following formulae:

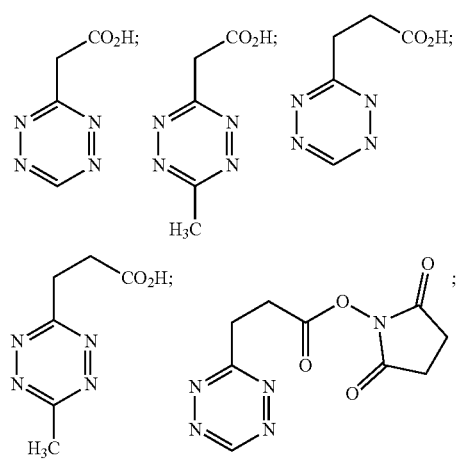

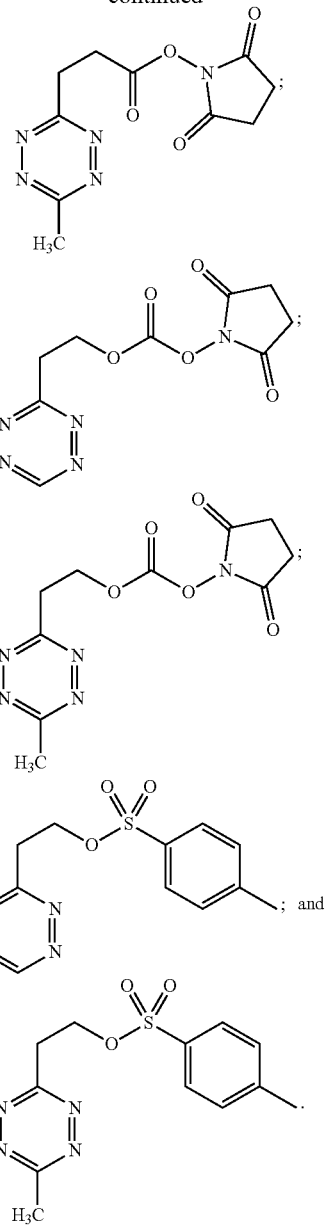

C. Compounds of Formula (III)

This disclosure provides compounds of formula (III):

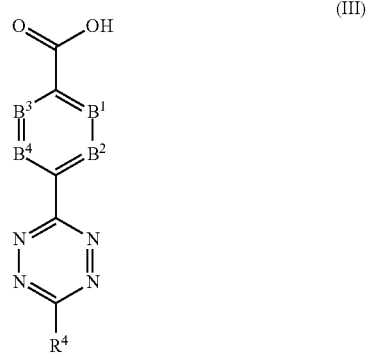

(III)

or a salt thereof, wherein:

$R^4$ is hydrogen or $(C_1-C_6)$alkyl, or substituted $(C_1-C_6)$alkyl;

$B^1$ is N, $B^2$ is CH, $B^3$ is N or CH, $B^4$ is N or CH; or
$B^1$ is CH, $B^2$ is N, $B^3$ is N or CH, $B^4$ is N or CH; or
$B^1$ is CH or $CR^5$, $B^2$ is CH or $CR^5$, $B^3$ is CH or $CR^5$ and $B^4$ is CH or $CR^5$; and each $R^5$ is halogen, nitro, or $CF_3$.

In some embodiments of the compounds of formula (III), no more than two of $B^1$, $B^2$, $B^3$ and $B^4$ are N.

In some embodiments of the compounds of formula (III), no more than three of $B^1$, $B^2$, $B^3$ and $B^4$ are CH.

In some embodiments of the compounds of formula (III), $R^4$ is hydrogen.

In some embodiments of the compounds of formula (III), $R^4$ is $(C_1-C_6)$alkyl.

In some embodiments of the compounds of formula (III), $R^4$ is methyl.

In some embodiments of the compounds of formula (III), $R^4$ is substituted $(C_1-C_6)$alkyl. The substituted $(C_1-C_6)$alkyl can be substituted, e.g., by 1, 2, 3, 4, or 5 substituents selected from $(C_2-C_6)$alkenyl, $(C_2-C_6)$alkynyl, halogen, $(C_1-C_6)$haloalkyl, —CN, —$NO_2$, —C(=O)R, —OC(=O)Ar, —C(=O)OR, —C(=O)$NR_2$, —C(=NR)$NR_2$, —OR, Ar, —OAr, —($(C_1-C_6)$alkylene)Ar, —O($(C_1-C_6)$alkylene)Ar, —OC(=O)$(C_1-C_6)$alkyl, —OC(=O)O$(C_1-C_6)$alkyl, —OC(=O)$NR_2$, —$NR_2$, —NRAr, —NR($(C_1-C_6)$alkylene)Ar, —NRC(=O)R, —NRC(=O)Ar, —NRC(=O)O$(C_1-C_6)$alkyl, —NRC(=O)$NR_2$, —$NRSO_2R$, —SR, —S(O)R, —$SO_2R$, —$OSO_2(C_1-C_6)$alkyl, —$SO_2NR_2$, —$(C_1-C_8)$perfluoroalkyl, —$(C_2-C_6)$alkylene-OR, —O$(C_2-C_6)$alkylene-N$((C_1-C_6)$alkyl$)_2$, —P(=O)(OR)$_2$, and —OP(=O)(OR)$_2$, wherein each R group is hydrogen or $(C_1-C_6$ alkyl), e.g., methyl and wherein each Ar is independently unsubstituted aryl or heteroaryl or aryl or heteroaryl substituted with one or more of $(C_1-C_6)$alkyl, $(C_2-C_6)$alkenyl, $(C_2-C_6)$alkynyl, halogen, $(C_1-C_6)$haloalkyl, —CN, —$NO_2$, —C(=O)R, —C(=O)OR, —C(=O)$NR_2$, —C(=NR)$NR_2$, —OR, —OC(=O)$(C_1-C_6)$alkyl, —OC(=O)O$(C_1-C_6)$alkyl, —OC(=O)$NR_2$, —$NR_2$, —NRC(=O)R, —NRC(=O)O$(C_1-C_6)$alkyl, —NRC(=O)$NR_2$, —$NRSO_2R$, —SR, —S(O)R, —$SO_2R$, —$OSO_2(C_1-C_6)$alkyl, —$SO_2NR_2$, $(C_1-C_8)$perfluoroalkyl, —$(C_2-C_6)$alkylene-OR, —O$(C_2-C_6)$alkylene-N$((C_1-C_6)$alkyl$)_2$, —P(=O)(OR)$_2$, —OP(=O)(OR)$_2$ wherein each R group is hydrogen or $(C_1-C_6$ alkyl). In some embodiments, the substituted $(C_1-C_6)$alkyl can be, e.g., substituted $(C_1-C_6)$haloalkyl.

In some embodiments of the compounds of formula (III), $B^1$ is N, $B^2$ is CH, $B^3$ is CH and $B^4$ is CH.

In some embodiments of the compounds of formula (III), $B^1$ is N, $B^2$ is CH, $B^3$ is N and $B^4$ is CH.

In some embodiments of the compounds of formula (III), $B^1$ is N, $B^2$ is CH, $B^3$ is CH and $B^4$ is N.

In some embodiments of the compounds of formula (III), $B^1$ is CH, $B^2$ is N, $B^3$ is CH and $B^4$ is CH.

In some embodiments of the compounds of formula (III), $B^1$ is CH, $B^2$ is N, $B^3$ is CH and $B^4$ is N.

In some embodiments of the compounds of formula (III), $B^1$ is CH or $CR^5$, $B^2$ is CH or $CR^5$, $B^3$ is CH or $CR^5$ and $B^4$ is CH or $CR^5$.

In some embodiments of the compounds of formula (III), $B^1$ is $CR^5$, $B^2$ is CH, $B^3$ is CH and $B^4$ is CH.

In some embodiments of the compounds of formula (III), $R^5$ is halogen.

In some embodiments of the compounds of formula (III), $R^5$ is fluorine.

Particular compounds according to formula (III) include compounds of the following formulae:

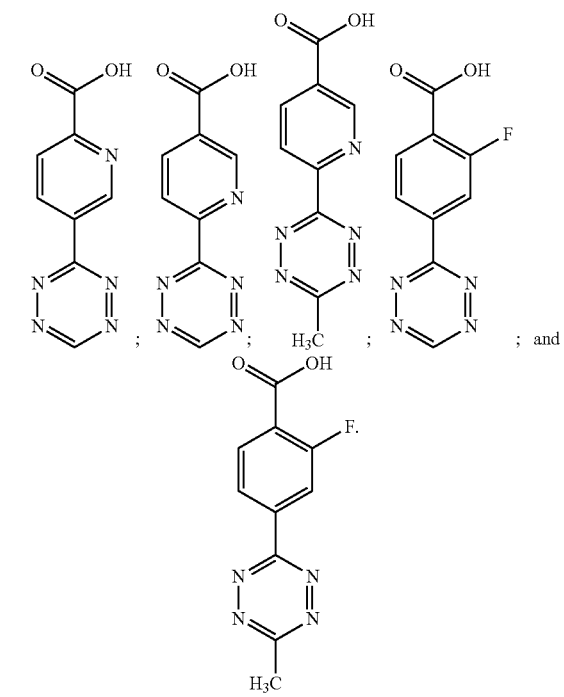

III. Synthesis

Compounds provided herein, including salts thereof, can be prepared using known organic synthesis techniques and can be synthesized according to any of numerous possible synthetic routes.

The reactions for preparing compounds as described herein can be carried out in suitable solvents which can be selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, e.g., in *Protecting Group Chemistry*, 1st Ed., Oxford University Press, 2000; *March's Advanced Organic chemistry: Reactions, Mechanisms, and Structure*, 5th Ed., Wiley Interscience Publication, 2001; Peturssion, S. et al., "Protecting Groups in Carbohydrate Chemistry," *J. Chem. Educ.*, 74(11), 1297 (1997), Wuts et al., *Protective Groups in Organic Synthesis*, 4th Ed., Wiley Interscience 2007.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UVvisible), mass spectrometry, or by chromatographic methods such as high performance liquid chromatography (HPLC), liquid chromatography mass spectroscopy (LCMS) or thin layer chromatography (TLC). Compounds can be purified by those skilled in the art by a variety of methods, including high performance liquid chromatography (HPLC) (Blom et al., *J. Combi. Chem.*, 2004, 6(6) 874-83) and normal phase silica chromatography.

In general, asymmetric 1,2,4,5-tetrazines can be prepared by a reaction according to the Scheme 2 shown below in which a nitrile, amidine, or imidate ester (R=an alkyl group) with hydrazine as solvent to generate a dihydrotetrazine. Asymmetric dihydrotetrazines are prepared by using two different precursors in a 5:1 ratio. Once generated, the initial dihydrotetrazines are oxidized to the 1,2,4,5-tetrazine by treatment with sodium nitrite under acidic conditions. The yield is typically in the range of about 4-25% overall yield.

Scheme 2

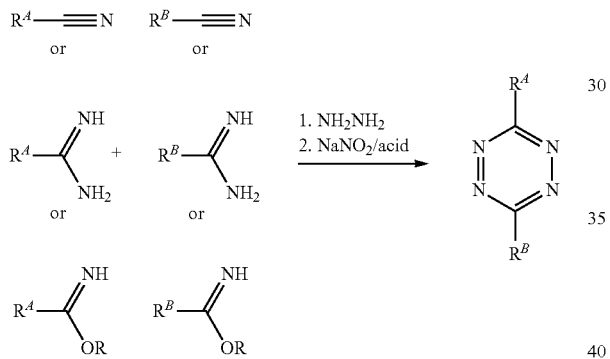

Thus, a compound of formula (I) can be prepared according to Scheme 3 shown below, in which a compound of formula (I-1) wherein $X^A$ is —CN, C(=NH)NH$_2$, or C(=NH)OR and R is an alkyl group (e.g., (C$_1$-C$_6$)alkyl, e.g., methyl or ethyl) is reacted with a compound according to formula (I-2) wherein $X^B$ is —CN, C(=NH)NH$_2$, or C(=NH)OR and R is an alkyl group (e.g., (C$_1$-C$_6$)alkyl, e.g., methyl or ethyl) to give the compound of formula (I).

Scheme 3

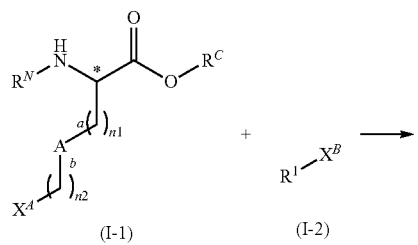

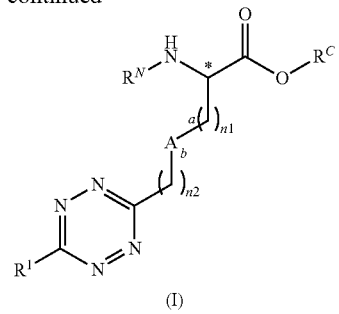

(I)

A compound of formula (I) wherein A is according to the formula (A2) can alternatively be prepared according to Scheme 4 shown below, in which a compound of formula (I-2) wherein $X^B$ is —CN, C(=NH)NH$_2$, or C(=NH)OR and R is an alkyl group (e.g., (C$_1$-C$_6$)alkyl, e.g., methyl or ethyl) is reacted with a compound of formula (I-3) wherein $X^A$ is —CN, C(=NH)NH$_2$, or C(=NH)OR and R is an alkyl group (e.g., (C$_1$-C$_6$)alkyl, e.g., methyl or ethyl) to give a 1,2,4,5-tetrazine of formula (I-4). The 1,2,4,5-tetrazine of formula (I-4) is then subjected to an amide bond coupling reaction with an amino acid derivative of formula (I-5) to form a compound according to Formula (I) wherein A is according to formula (A2).

Scheme 4

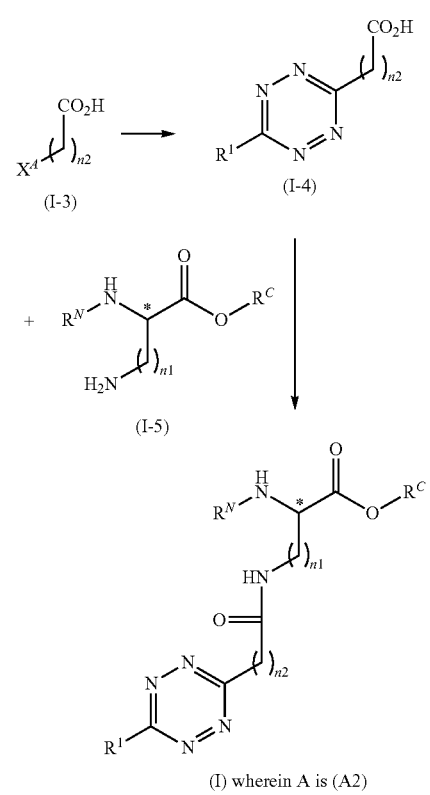

Amide coupling reactions are known in the art and can be carried out under mild conditions with a variety of agents, e.g., N,N'-diisopropyl azidodicarboxylate; N,N'-diisopropylcarbodiimide; 1-ethyl-3-(3-dimethylaminopropyl) carbodiimide), O-(7-azabenzotriazol-1-yl)-N,N,N',N'-tetramethyluronium hexafluorophosphate. The coupling chemistry may involve the intermediate formation of an activated ester, e.g., with HOBt (N-hydroxybenzotriazole) or N-hydroxysuccinimide. See, e.g., *Peptide Synthesis*, Chemfiles, Sigma Aldrich, Vol. 7 No. 2 (2007).

A compound of formula (I) wherein A is according to the formula (A3) can alternatively be prepared according to Scheme 4 shown below, in which a compound of formula (I-2) wherein $X^B$ is —CN, C(=NH)NH$_2$, or C(=NH)OR and R is an alkyl group (e.g., (C$_1$-C$_6$)alkyl, e.g., methyl or ethyl) is reacted with a compound of formula (I-6) wherein $X^A$ is —CN, C(=NH)NH$_2$, or C(=NH)OR and R is an alkyl group (e.g., (C$_1$-C$_6$)alkyl, e.g., methyl or ethyl) to give a 1,2,4,5-tetrazine of formula (I-7). The 1,2,4,5-tetrazine of formula (I-7) is then reacted with a suitable carbonylating agent of the formula (I-8) in which each L is a suitable leaving group to give a compound of formula (I-9). Suitable carbonylating agents include, e.g., disuccinimidyl carbonate, in which each L is a N-oxysuccinimide group. The compound of formula (I-9) is then reacted with an amino acid derivative of formula (I-5) to form a compound according to Formula (I) wherein A is according to formula (A3).

Scheme 5

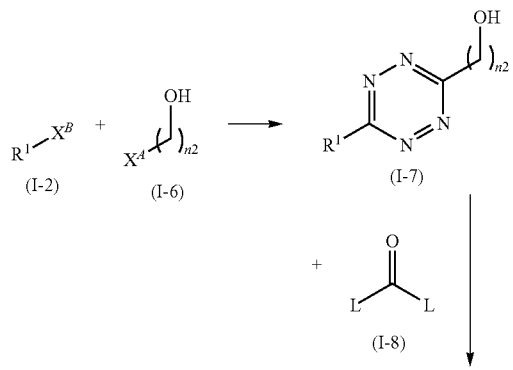

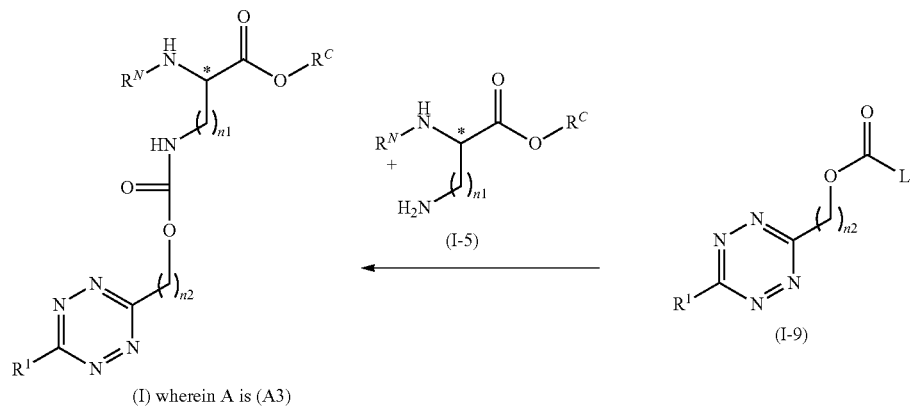

A compound of formula (I) wherein A is according to the formula (A4) can alternatively be prepared according to Scheme 6 shown below, in which a compound of formula (I-2) wherein $X^B$ is —CN, C(=NH)NH$_2$, or C(=NH)OR and R is an alkyl group (e.g., (C$_1$-C$_6$)alkyl, e.g., methyl or ethyl) is reacted with a compound of formula (I-10) wherein $X^A$ is —CN, C(=NH)NH$_2$, or C(=NH)OR and R is an alkyl group (e.g., (C$_1$-C$_6$)alkyl, e.g., methyl or ethyl) to give a 1,2,4,5-tetrazine of formula (I-11). The compound of formula (I-11) is then subjected to an amide bond coupling reaction with an amino acid derivative of formula (I-12) to form a compound according to Formula (I) wherein A is according to formula (A4).

Scheme 6

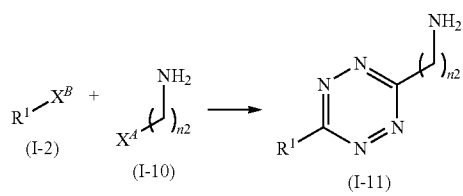

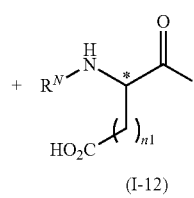

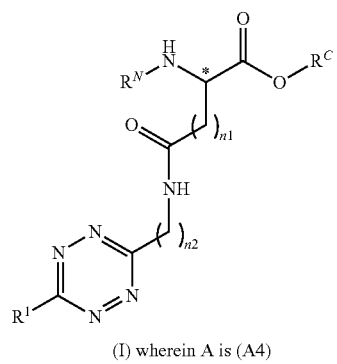

(I) wherein A is (A4)

A compound of formula (I) wherein A is according to the formula (A5) can alternatively be prepared according to Scheme 7 shown below, in which a compound of formula (I-2) wherein $X^B$ is —CN, C(=NH)NH$_2$, or C(=NH)OR and R is an alkyl group (e.g., (C$_1$-C$_6$)alkyl, e.g., methyl or ethyl) is reacted with a compound of formula (I-13) wherein $X^A$ is —CN, C(=NH)NH$_2$, or C(=NH)OR and R is an alkyl group (e.g., (C$_1$-C$_6$)alkyl, e.g., methyl or ethyl) to give a 1,2,4,5-tetrazine of formula (I-14). The compound of formula (I-14) is then subjected to an amide bond coupling reaction with an amino acid derivative of formula (I-5) to form a compound according to Formula (I) wherein A is according to formula (A5).

Scheme 7

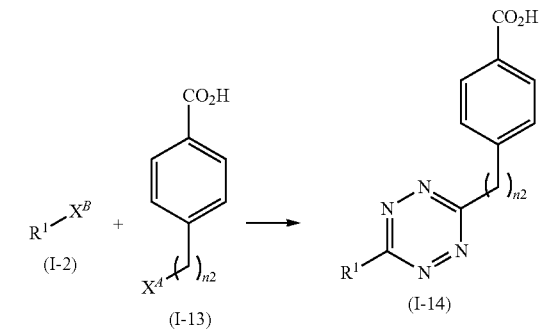

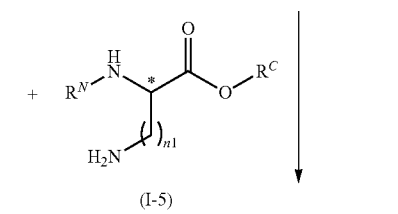

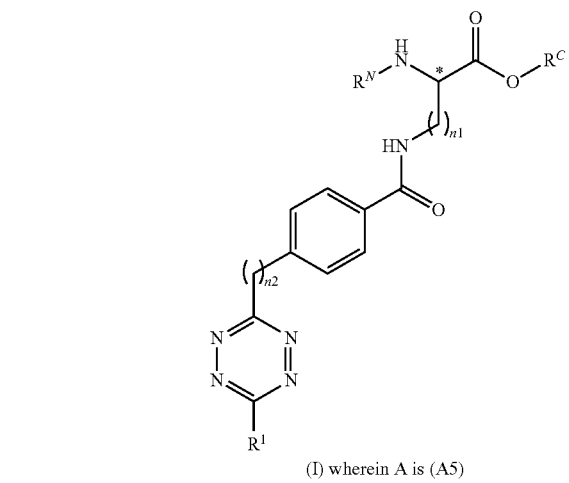

(I) wherein A is (A5)

A compound of formula (II) can be prepared according to Scheme 8 shown below, in which a compound of formula (II-1) wherein $X^C$ is —CN, C(=NH)NH$_2$, or C(=NH)OR and R is an alkyl group (e.g., (C$_1$-C$_6$)alkyl, e.g., methyl or ethyl) is reacted with a compound according to formula (II-2) wherein XD is —CN, C(=NH)NH$_2$, or C(=NH)OR and R is an alkyl group (e.g., (C$_1$-C$_6$)alkyl, e.g., methyl or ethyl) to give the compound of formula (II). If necessary, R$^3$ can be carried through the 1,2,4,5-tetrazine formation in protected form or alternatively a precursor group to R$^3$ may be employed (i.e., a functional group which can be subsequently converted to form the group R$^3$ through a functional group transformation reaction).

Scheme 8

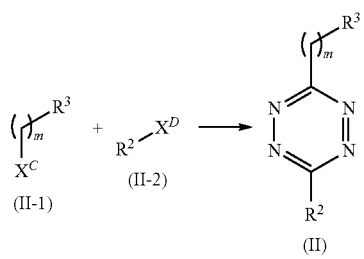

A compound of formula (III) can be prepared according to Scheme 8 shown below, in which a compound of formula (III-1) wherein $X^E$ is —CN, C(=NH)NH$_2$, or C(=NH)OR and R is an alkyl group (e.g., (C$_1$-C$_6$)alkyl, e.g., methyl or ethyl) is reacted with a compound according to formula (III-2) wherein $X^F$ is —CN, C(=NH)NH$_2$, or C(=NH)OR and R is an alkyl group (e.g., (C$_1$-C$_6$)alkyl, e.g., methyl or ethyl) to give the compound of formula (III).

Scheme 9

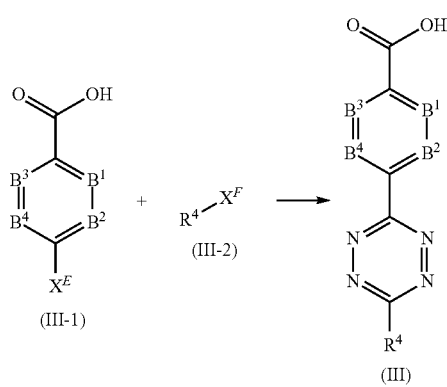

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds described herein may be synthesized and that a broad repertoire of synthetic organic reactions is available to be potentially employed in synthesizing compounds described herein. For example, if a group is incompatible with the chemistry described it can be protected with a protected group or carried through as a precursor group and subsequently converted to the desired functional group through an appropriate functional group transformation. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. MethCohn and C. W. Rees (Pergamon Press, 1996), *Comprehensive Organic Functional Group Transformations II*, Ed. A. R. Katritzky and R. J. K. Taylor (Editor) (Elsevier, 2$^{nd}$ Edition, 2004), *Comprehensive Heterocyclic Chemistry*, Ed. A. R. Katritzky and C. W. Rees (Pergamon Press, 1984) and *Comprehensive Heterocyclic Chemistry II*, Ed. A. R. Katritzky, C. W. Rees and E. F. V. Scriven (Pergamon Press, 1996).

To incorporate the compounds described above into ligand and payload compounds for bioorthogonal coupling chemistry, as further described below, standard methods of chemical synthesis may be used. For incorporating the amino acid compounds described herein into peptides, proteins and polypeptides, methods of peptide synthesis are used.

Methods of synthesizing amino acids and peptides which may be useful in preparing compounds according to the present disclosure and incorporating such compounds as building into ligand and payload compounds are described, e.g., by: Benoiton, *Chemistry of Peptide Synthesis*, CRC Press, 2006; Hughes, et al., *Amino Acids, Peptides and Proteins in Organic Chemistry*, Vol. 1, *Origins and Synthesis of Amino Acids*, Wiley-VCH 2009; Hughes, et al., *Amino Acids, Peptides and Proteins in Organic Chemistry*, Vol. 2. *Modified Amino Acids, Organocatalysis and Enzymes*; Wiley-VCH 2010; Hughes, et al., *Amino Acids, Peptides and Proteins in Organic Chemistry* Vol. 3: *Building Blocks, Catalysis and Coupling Chemistry*, Wiley-VCH 2011; Hughes, et al., *Amino Acids, Peptides and Proteins in Organic Chemistry*, Vol. 4: *Amino Acids, Peptides and Proteins in Organic Chemistry, Protection Reactions, Medicinal Chemistry, Combinatorial Synthesis*, Wiley-VCH 2011; *Amino Acids, Peptides and Proteins in Organic Chemistry*, Vol. 5: *Amino Acids, Peptides and Proteins in Organic Chemistry, Analysis and Function of Amino Acids and Peptides*, Wiley-VCH 2011; Howl, et al., *Peptide Synthesis and Applications (Methods in Molecular Biology* Vol. 298), Humana Press, 2010; Jones, *Amino Acid and Peptide Synthesis*, 2nd Ed., Oxford University Press, 2002; Jones, *The Chemical Synthesis of Peptides (International Series of Monographs on Chemistry)*, Oxford University Press, 1994; Pennington, et al., *Peptide Synthesis Protocols (Methods in Molecular Biology* Vol. 35), Humana Press, 1994; Sewald, et al., *Peptides: Chemistry and Biology*, Wiley-VCH, 2009; Williams, et al., *Chemical Approaches to the synthesis of Peptides and Proteins (New Directions in Organic & Biological Chemistry)*, CRC Press 1997.

IV. Methods of Use

The compounds described herein may be used in methods such as those described in WO2010/051530 for delivering a "payload," such as a therapeutic or detectable agent, to a biological target. These methods include the use of bioorthogonal chemistry to achieve bioconjugation using the inverse electron demand Diels-Alder reaction to deliver a payload, such as a therapeutic or detectable compound, using specific ligands such as antibodies, small molecules and other biomolecules. The specific ligand is attached, optionally through a linker, to one component of the Diels-Alder pair, and the payload is attached, also optionally through a linker, to the other component. For example, if the ligand is attached to a 1,2,4,5-tetrazine diene, then the payload is attached to a dienophile (e.g., trans-cyclooctene); if the ligand is attached to the dienophile, then the payload is attached to the 1,2,4,5-tetrazine diene. The methods and compositions can be used, e.g., in vivo and in vitro, both extracellularly or intracellularly, as well as in assays such as cell free assays.

In particular, as described in more detail below, the compounds described herein are functionalized 1,2,4,5-tetrazine compounds that are useful to attach the 1,2,4,5-tetrazine diene moiety, to either the ligand molecule or to the payload molecule.

Biological Targets

The methods and compositions described herein can be used to deliver a payload to any biological target for which a specific ligand exists or can be generated. The ligand can bind to the target either covalently or non-covalently.

Exemplary biological targets include biopolymers, e.g., proteins, nucleic acids, or polysaccharides; exemplary proteins include enzymes, receptors and ion channels; other exemplary targets include small molecules, e.g., lipids, phospholipids, sugars, peptides, hormones, or neurotransmitters. In some embodiments the target is a tissue- or cell-type specific marker, e.g., a protein that is expressed specifically on a selected tissue or cell type. In some embodiments, the target is a receptor, such as, but not limited to, plasma membrane receptors and nuclear receptors; more specific examples include ligand-gated ion channels, G-protein-coupled receptors, and growth factor receptors. In one embodiment, the receptor is an epidermal growth factor receptor (EGFR).

Ligands

A ligand can be any compound, such as a small molecule or biomolecule (e.g., an antibody or antigen-binding fragment thereof), that binds specifically to a selected target, and can be functionalized by the addition of a 1,2,4,5-tetrazine diene or dienophile, optionally via a linker.

Antibodies

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind antigen. Such fragments can be obtained commercially, or using methods known in the art. For example F(ab)2 fragments can be generated by treating the antibody with an enzyme such as pepsin, a non-specific endopeptidase that normally produces one F(ab)2 fragment and numerous small peptides of the Fc portion. The resulting F(ab)2 fragment is composed of two disulfide-connected Fab units. The Fc fragment is extensively degraded and can be separated from the F(ab)2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,000 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region.

In addition to utilizing whole antibodies, the disclosure encompasses the use of binding portions of such antibodies. Such binding portions include Fab fragments, F(ab')2 fragments, and Fv fragments. These antibody fragments can be made by conventional procedures, such as proteolytic fragmentation procedures, as described in Goding, *Monoclonal Antibodies: Principles and Practice*, pp. 98-118 (N.Y. Academic Press 1983).

Chimeric, humanized, de-immunized, or completely human antibodies are desirable for applications which include repeated administration, e.g., therapeutic treatment of human subjects.

The antibody can also be a single chain antibody. A single-chain antibody (scFV) can be engineered (see, e.g., Colcher et al., *Ann. N. Y. Acad. Sci.*, 1999, 880, 263-80; and Reiter, *Clin. Cancer Res.*, 1996, 2, 245-52. The single chain antibody can be dimerized or multimerized to generate multivalent antibodies having specificities for different epitopes of the same target protein. In some embodiments, the antibody is monovalent, e.g., as described in Abbs et al., *Ther. Immunol.*, 1994, 1(6), 325-31.

Methods for making suitable antibodies are known in the art. See, e.g., Harlow et al. (Eds.), *Antibodies: A Laboratory Manual* (Cold Spring Harbor Laboratory Press 1988).

In some embodiments, the antibody binds specifically to a tumor antigen, or to an antigen present in a tissue in which a tumor is present. A number of antibodies against cancer-related antigens are known. Ross et al., *Am. J. Clin. Pathol.*, 2003, 119(4):472-485. Examples include Alemtuzumab (Campath); Daclizumab (Zenapax); Rituximab (Rituxan); Trastuzumab (Herceptin); Gemtuzumab (Mylotarg); Ibritumomab (Zevalin); Edrecolomab (Panorex); Tositumomab (Bexxar); CeaVac; Epratuzumab (LymphoCide); Mitumomab; Bevacizumab (Avastin); Cetuximab (C-225; Erbitux); Edrecolomab; Lintuzumab (Zamyl); MDX-210; IGN-101; MDX-010; MAb, AME; ABX-EGF; EMD 72 000; Apolizumab; Labetuzumab; ior-t1; MDX-220; MRA; H-11 scFv; Oregovomab; huJ591 MAb, BZL; Visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; H22xKI-4; ABX-MA1; Imuteran; and Monopharm-C. In some embodiments in which the ligand is specific for a tumor antigen or cancerous tissue, the payload can be a therapeutic agent such as a cytotoxin, radioactive agent, or other therapeutic agent useful in treating cancer.

Small Molecules and Biomolecules

Small molecules are low molecular weight organic compounds (typically less than about 2000 Daltons). Small molecules useful in the compositions and methods described herein bind with high affinity to a biopolymer, such as protein, nucleic acid, or polysaccharide, or other biological target. Useful small molecules are capable of being functionalized with a dienophile or a 1,2,4,5-tetrazine diene. For example, a small molecule can be an agent such as taxol, which binds specifically to microtubules and is capable of being functionalized with a dienophile such as trans-cyclooctene or another alkene. Other examples include small molecules that bind specifically to receptors for hormones, cytokines, chemokines, or other signaling molecules. Small molecules include peptides.

Biomolecules are organic molecules produced by living organisms, including large polymeric molecules such as polypeptides, proteins, polysaccharides, and nucleic acids as well as small molecules such as primary metabolites, secondary metabolites, and natural products. Specific small molecule examples include, but are not limited to, estradiol, testosterone, cholesterol, phosphatidylserine or phosphatidylcholine.

Linker

The term "linker" as used herein refers to a group of atoms, e.g., 0-500 atoms, and may be comprised of the atoms or groups such as, but not limited to, carbon, amino, alkylamino, oxygen, sulfur, sulfoxide, sulfonyl, carbonyl, and imine. The linker chain may also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers. The linker must not interfere with binding of the ligand to the target, or with the Diels-Alder reaction.

In its simplest form, a linker can be a covalent chemical bond. In other embodiments, the linker can be a chemical group. Since the function of the linking group is merely to provide a physical connection, a wide variety of chemical groups can serve as linking groups. A linker is typically a divalent organic linking group where one valency represents the point of attachment to ligand or payload molecule and one valency represents the attachment to the 1,2,4,5-tetrazine or dienophile. The only requirement for the linker is to provide a stable physical linkage that is compatible with maintaining the function of the ligand or payload molecule and is compatible with the Diels Alder chemistry.

Examples of suitable linking groups include, e.g.: —O—, —S—, —S(O)—, —S(O)$_2$—, —C(O)—, —NH—, —N(C$_1$-C$_6$)alkyl, —NHC(O)—, —C(O)NH—, —O(CO)—, —C(O)O—, —O(CO)NH—, —NHC(O)O—, —O(CO)O—, —NHC(O)NH—, —O(C$_1$-C$_6$)alkylene-, —S(C$_1$-C$_6$)alkylene-, —S(O)(C$_1$-C$_6$)alkylene-, —S(O)$_2$(C$_1$-C$_6$)alkylene-, —C(O)(C$_1$-C$_6$)alkylene-, —NH((C$_1$-C$_6$)alkylene)C(O)—, —C(O)((C$_1$-C$_6$)alkylene)C(O)—, —C(O)((C$_1$-C$_6$)alkylene)NH—, —O(CO)—, —C(O)O—, —O(CO)NH—, —NHC(O)O—, —O(CO)O—, —NHC(O)NH—, unsubstituted-(C$_1$-C$_{10}$)alkylene-, unsubstituted-(C$_1$-C$_{10}$)heteroalkylene, or —(C$_1$-C$_{10}$)alkylene or —(C$_1$-C$_{10}$)heteroalkylene substituted with one or more (e.g., 1, 2, 3, 4 or 5 substituents) independently selected from the group consisting of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_1$-C$_6$)alkylene)Ar, —O((C$_1$-C$_6$)alkylene)Ar, —OC(=O)(C$_1$-C$_6$)alkyl, —OC(=O)O(C$_1$-C$_6$)alkyl, —OC(=O)NR$_2$, —NR$_2$, —NRAr, —NR((C$_1$-C$_6$)alkylene)Ar, —NRC(=O)R, —NRC(=O)Ar, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$, oxo and sulfido, wherein each R group is hydrogen or (C$_1$-C$_6$ alkyl), e.g., methyl and wherein each Ar is independently unsubstituted aryl or heteroaryl or aryl or heteroaryl substituted with one or more of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —C(=O)OR, —C(=O)NR$_2$, —C(=NR)NR$_2$, —OR, —OC(=O)(C$_1$-C$_6$)alkyl, —OC(=O)O(C$_1$-C$_6$)alkyl, —OC(=O)NR$_2$, —NR$_2$, —NRC(=O)R, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$ wherein each R group is hydrogen or (C$_1$-C$_6$ alkyl). In addition, —(C$_1$-C$_{10}$)alkylene- and —(C$_1$-C$_{10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$O—, where n is an integer, e.g., 1, 2, 3, 4 or 5). The —(C$_1$-C$_{10}$)alkylene- and —(C$_1$-C$_{10}$)heteroalkylene also include —(C$_1$-C$_6$)alkylene- and —(C$_1$-C$_6$)heteroalkylene and —(C$_1$-C$_3$)alkylene- and —(C$_1$-C$_3$)heteroalkylene.

Diels-Alder Pairs

The methods described herein include the use of Diels-Alder pairs that include a 1,2,4,5-tetrazine as a diene and a suitable dienophile. The inverse electron demand Diels-Alder cycloaddition reaction of a 1,2,4,5-tetrazine with a dienophile (e.g., an alkene or alkyne), produces an unstable cycloadduct which subsequently undergoes a retro-Diels-Alder cycloaddition reaction to produce nitrogen as a byproduct and the desired dihydropyrazine (after reaction with an alkene) or pyrazine (after reaction with an alkyne) products (Scheme 1). The dihydropyrazine product may undergo an additional oxidation step to generate the corresponding pyrazine.

Bioorthogonal Chemistry

Bioconjugation methods using inverse electron demand Diels-Alder cycloadditions between 1,2,4,5-tetrazines and highly strained dienophiles such as norbornene and trans-cyclooctene are known in the literature. Blackman et al., *J. Am. Chem. Soc.*, 2008, 130, 13518-19; Devaraj et al., *Angew. Chem. Int. Ed. Engl*, 2009, 48, 7013-6; Devaraj et al., *Bioconjug. Chem.*, 2008, 19, 2297-99; Pipkorn et al., *J. Pept. Sci.*, 2009, 15, 235-41. 1,2,4,5Tetrazines can be unstable in solution, but can react rapidly at 37° C. with strained alkenes such as trans-cyclooctene. Devaraj et al., *Angew. Chem. Int. Ed. Engl.*, 2009, 48, 7013-16. This extremely fast reaction allows for the labeling of extracellular targets at low nanomolar concentrations of 1,2,4,5-tetrazine labeling agent, concentrations that are sufficiently low to allow for real-time imaging of probe accumulation.

The bioorthogonal inverse electron demand Diels-Alder reaction of 1,2,4,5-tetrazines can be tailored to provide a straightforward method for the rapid, specific covalent labeling and imaging with ligands such as small molecules and other biomolecules inside living cells. The labeling can be performed as shown in FIG. 1.

In the labeling scheme of FIG. 1, a specific ligand, e.g., an antibody, small molecule or other biomolecule, is physically attached to a first Diels-Alder component that is either a 1,2,4,5-tetrazine or a dienophile that is capable of rapid, specific reaction with a 1,2,4,5-tetrazine. In some embodiments, the ligand carries a functional group such as an amine, alcohol, carboxylic acid or ester, or other group of atoms on the ligand that can undergo a chemical reaction allowing attachment to the Diels Alder component, and the Diels Alder component that functional group to allow attachment to the ligand. A chemical reaction can be attached to the ligand. In some embodiments, the attachment can be by way of a linking group that is covalently attached to both the biomolecule and the first Diels-Alder component. In some embodiments, where the ligand is a biopolymer, such as a nucleic acid, peptide, or polypeptide, the functional group on the ligand can be a non-natural nucleoside or amino acid that has been incorporated into the structure of the polypeptide and the 1,2,4,5-tetrazine group or a dienophile is incorporated into the side chain of the non-natural amino acid. The non-natural amino-acid can be incorporated, e.g., using methods known in the art of synthesizing peptides (e.g., solid phase synthesis methods), which are discussed in greater detail below.

A second compound, a payload compound, such as a therapeutic agent or a detectable agent, which it to be delivered into the cell in proximity to the biological target, is labeled with a second Diels-Alder component, complementary to the first, such that the first and second Diels-Alder component are capable of undergoing an inverse-electron-demand Diels Alder reaction. Thus if the first Diels Alder component is a 1,2,4,5-tetrazine, the second Diels Alder component is a dienophile such as a trans-cyclooctene, and vice versa.

The procedure for introducing the payload molecule into the cell using the bioorthogonal chemistry thus involves, as a first step, incubating the ligand comprising the first Diels-Alder component in the presence of the biological target, whereupon selective binding of the ligand to the biological target occurs. The payload molecule that comprises the second Diels-Alder component is then added. The first and second Diels-Alder components then undergo an inverse-electron-demand Diels-Alder reaction to deliver the payload to the proximity of the biological target. Specifically, the payload becomes covalently attached to the ligand by virtue of the inverse-electron-demand Diels-Alder reaction.

Dienes

The compounds described herein, or any of the embodiments thereof, can be used to attach the 1,2,4,5-tetrazine moiety contained within the molecule to either the ligand or payload. The compounds described herein may be attached to the ligand or payload through reacting the compound with an accessible functional group of the ligand or payload using a suitable chemical transformation that forms a covalent bond, optionally via a linking group. For example, if the compound has a free amino group and the ligand or payload compound has an accessible carboxyl group, then the 1,2,4,5-tetrazine can be attached to the ligand or payload, e.g., by using an amide coupling reaction. Similarly if the compound contains a free carboxyl group and the ligand or payload compound has an accessible amino group, then the 1,2,4,5-tetrazine can be attached to the ligand or payload, e.g., again by using an amide coupling reaction. If the compound has a leaving group and the ligand or payload compound has an accessible nucleophilic group (e.g., an amino, mercaptan, or hydroxyl group), then the 1,2,4,5-tetrazine can be attached to the ligand or payload, e.g., by using an nucleophilic displacement reaction. In addition, the 1,2,4,5-tetrazine can be attached to the ligand or payload by using a compound described herein as a chemical building block in the synthesis of the ligand or payload. The compounds described herein that are amino acids can be incorporated into peptides using standard methods of peptide synthesis. A suitable ligand or payload compound can be based on a known peptide modified so as to replace one of its amino acids by one of the 1,2,4,5-tetrazine-containing amino acids described herein. The site of substitution and the selection of the 1,2,4,5-tetrazine-containing amino acids can be based on the structure-activity relationships of the relevant peptide. The 1,2,4,5-tetrazine-containing amino acid can, e.g., replace an amino acid whose activity is not essential to the desired biological activity (e.g., target binding) of a ligand or payload compound that is a peptide and "conservative" modifications can be made, where one of the peptides of a known ligand or payload compound is replaced by a 1,2,4,5-tetrazine-containing amino acid that has, so far as possible, a reasonably similar chemical structure to the peptide which is replaced.

Dienophiles

Dienophiles useful in the present methods and compositions include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g., sytrenes) and/or electron rich electrophiles (e.g., enamines or vinyl ethers), can also be used with nitroso compounds. Alkenes can include an alkyl group having one or more double carbon-carbon bonds such as an ethylene, propylene, and the like. Alkenes can also include cyclic, ring-strained alkenes such as trans-cyclooctene or norbornene carrying a double bond which induces significant ring strain and is thus highly reactive. Alkenes can also include more complex structures such as indoles and azaindoles, electron rich enamines. Heterodienophiles containing carbonyl, nitroso or imine groups can also be used. In some preferred embodiments, the dienophile is a trans-cyclooctene, e.g., a trans-cyclooctenol, e.g., (E)-cyclooct-4-enol. Other groups that undergo rapid reaction with 1,2,4,5-tetrazines include cyclooctyne groups.

Examples of known compounds that are suitable to attach a trans-cyclooctene group to a ligand or payload compound include the known compounds of the following structures:

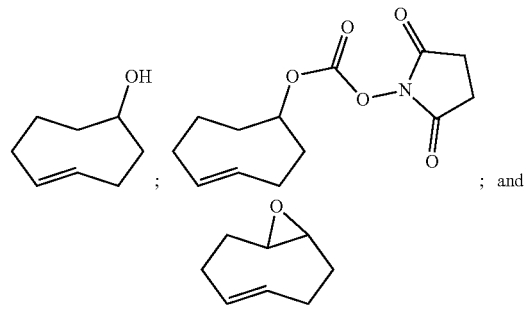

; and

Payload

The methods and compositions described herein are useful for delivering a payload to a biological target. The payload can be used, e.g., for labeling (e.g, a detectable agent such as a fluorophore), or for therapeutic purposes (e.g., a cytotoxin or other therapeutic agent).

Therapeutic Agents

In some embodiments the payload is a therapeutic agent such as a cytotoxin, radioactive ion, or other therapeutic agents. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Nucleic acids, e.g., inhibitory nucleic acids, e.g., small interfering RNAs, antisense, aptamers, can also be used as therapeutic agents.

Detectable Agents

Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Examples of suitable enzymes include horseradish peroxidase, alkaline phosphatase, β-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl) aminohexanoic acid, succinimidyl ester (BODIPY® 650/665-X), 7-N,N'-diethylaminocoumarin, VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, or $^{3}$H, $^{99m}$Tc (e.g, as pertechnetate (technetate(VII), TcO$_4$) either directly or indirectly, or other radioisotope detectable by direct counting of radioemission or by scintillation counting. In addition, contrast agents, e.g., contrast agents for MRI or NMR, for X-ray CT, Raman imaging, optical coherence tomogrpahy, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic 1,2,4,5-tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical)).

When the compounds are enzymatically labeled with, e.g., horseradish peroxidase, alkaline phosphatase, or luciferase, the enzymatic label is detected by determination of conversion of an appropriate substrate to product.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Cell Penetrating Moieties and Agents

In some embodiments the compositions also include a cell penetrating moiety or agent that enhances intracellular delivery of the compositions. For example, the compositions can include a cell-penetrating peptide sequence that facilitates delivery to the intracellular space, e.g., HIV-derived TAT peptide, penetratins, transportans, or hCT derived cell-penetrating peptides, see, e.g., Caron et al., *Mol. Ther.*, 2001, 3(3), 310-18; Deshayes et al., *Cell. Mol. Life Sci.*, 2005, 62(16), 1839-49; El-Andaloussi et al., *Curr. Pharm. Des.*, 2005, 11(28), 3597-611; Langel, *Cell-Penetrating Peptides: Processes and Applications*, CRC Press, Boca Raton Fla. (2002). The compositions can also be formulated to include a cell penetrating agent, e.g., liposomes, that enhances delivery of the compositions to the intracellular space.

Applications

The compositions and methods described herein can be used in a number of different scenarios in which delivery of a substance (the "payload") to a biological target is desired, e.g., delivery of detectable substances for detection of the target, or delivery of a therapeutic agent. Detection methods can include both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

As one example, the Diels-Alder coupling reaction as described herein can be used in place of standard avidin (or streptavidin)/biotin coupling procedures. Many tissue types may contain endogenous biotin, so with the current standard biotin-based coupling procedures, an additional step to block the activity of the endogenous biotin may be necessary to eliminate unwanted non-specific background staining. This blocking step is not necessary if the compositions described herein are used.

This procedure is also used for electron microscopy where the fluorophore-dienophile (or -diene) component is replaced by a gold nanoparticle-dienophile (or -diene) conjugate.

The Diels-Alder coupling compositions described herein should also be applicable to any in situ hybridization (ISH) or fluorescence in situ hybridization (FISH) protocol for visualization of DNA or RNA in tissue or cell preparations in which the avidin (streptavidin)/biotin system is employed, e.g., Tyramide Signal Amplification FISH.

The Diels-Alder coupling reaction as described herein can also be used as an alternative to secondary antibodies or in place of standard avidin (or streptavidin)/biotin coupling procedures during a western blot.

In addition, the compositions described herein can be used to deliver therapeutic agents to cells or tissues, e.g., in living animals. Thus a therapeutic compound is attached to one half of the Diels-Alder pair, and a ligand that targets the desired cell or tissue is attached to the other half. For example, a ligand such as an antibody that recognizes a tumor cell is attached to one half, and the other half is linked to a payload comprising a cytotoxin, e.g., a toxin or radioactive substance.

These compositions are particularly useful for pretargeting strategies where the ligand has a long half life in the body. For example, monoclonal antibodies have a very long half-life in the blood. This property leads to poor target-to-background ratios when the antibodies are labeled directly with imaging agents or cytotoxins. See, e.g., Wu et al., *Nat. Biotechnol.*, 2005, 23, 1137-46. The methods and compositions described herein can circumvent these problems.

Pharmaceutical Compositions and Methods of Administration

The methods described herein include the manufacture and use of pharmaceutical compositions, which include compounds described herein as active ingredients. Also included are the pharmaceutical compositions themselves. In some embodiments, the compositions include a ligand that is specific for a tumor antigen or cancerous tissue, and the payload is a therapeutic agent such as a cytotoxin, radioactive agent, or other therapeutic agent useful in treating cancer.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, e.g., water, ethanol, polyol (for example, glycerol, propylene glycol, and liquid polyetheylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal agents, e.g., parabens, chlorobutanol, phenol, ascorbic acid, thimerosal, and the like. In many cases, it will be preferable to include isotonic agents, e.g., sugars, polyalcohols such as mannitol, sorbitol, sodium chloride in the composition. Prolonged absorption of the injectable compositions can be brought about by including in the composition an agent that delays absorption, e.g., aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, e.g., as described in U.S. Pat. No. 4,522,811.

The pharmaceutical compositions can be included in a container, pack, or dispenser together with instructions for administration.

EXAMPLES

Example 1. General Synthetic Method for the Synthesis of 1,2,4,5-Tetrazines 1,2,4,5-Tetrazines may be prepared by reaction of a nitrile, amidine, or imidate ester with hydrazine as solvent to generate a dihydrotetrazine. Asymmetric dihydrotetrazines are prepared by using two different precursors in a 5:1 ratio. Once generated, the initial dihydrotetrazines are oxidized to the tetrazine by treatment with sodium nitrite under acidic conditions. The yield is typically in the range of about 4-25% overall yield.

Example 2. 2-((tert-Butoxycarbonyl)amino)-3-(4-(6-methyl-1,2,4,5-tetrazin-3-yl)phenyl)propanoic acid (N-(tert-Butoxycarbonyl)-4-(6-methyl-1,2,4,5-tetrazin-3-yl)phenylalanine)

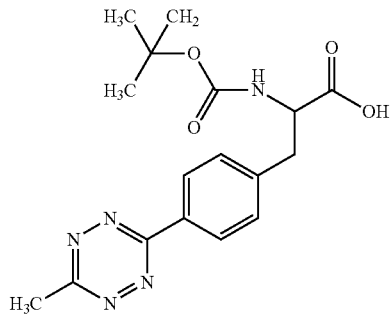 [SMILES: Cc1nnc(-c2ccc(CC(NC(=O)OC(C)(C)C)C(=O)O)cc2)nn1]

2-((tert-Butoxycarbonyl)amino)-3-(4-cyanophenyl)propanoic acid (N-(tert-butoxycarbonyl)-4-cyaanophenylalanine) 1.84 g (6.3 mmol) was mixed with 10 molar equivalents of MeCN (3.326 mL) and 5 mol % zinc triflate (1.268 g). Hydrazine monohydrate (6.76 mL, 140 mmol) was then added and the reaction was stirred at 70° C. for 90 min. To the cooled reaction mixture was added 63 mmol NaNO$_2$ in 20 mL water followed by 2% aqueous HCl (~250 mL). The acidic solution was then saturated with NaCl and extracted with DCM (3×150 mL). The organic layer was then dried with MgSO$_4$, filtered, and lyophilized to dryness. The crude product mixture was then purified by column chromatography, eluting with 10:1:0.1%, DCM:acetone:formic acid yielding a pink-red solid (24% yield). ESI-MS calc. for C$_{17}$H$_{20}$N$_5$O$_4$$^+$ 358.15; found 358.2. $^1$H NMR (DMSO-d$_6$) δ 12.7 (1H, br s), 8.38 (2H, d, J=8.5 Hz), 7.54 (2H, d, J=8.5 Hz), 7.21 (1H, d, J=8.5 Hz), 4.19 (1H, m), 3.15 (1H, dd, J=14.0, 4.5 Hz), 3.01-2.94 (4H, m).

Example 3. 2-Amino-3-(4-(6-methyl-1,2,4,5-tetrazin-3-yl)phenyl)propanoic acid (4-(6-Methyl-1,2,4,5-tetrazin-3-yl)phenylalanine)

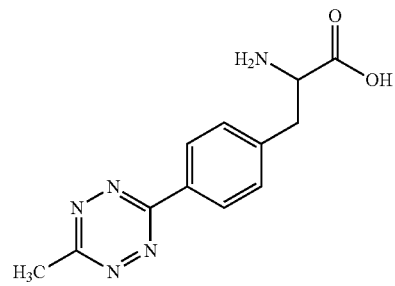 [SMILES: Cc1nnc(-c2ccc(CC(N)C(=O)O)cc2)nn1]

2-((tert-Butoxycarbonyl)amino)-3-(4-(6-methyl-1,2,4,5-tetrazin-3-yl)phenyl)propanoic acid (N-(tert-butoxycarbonyl)-4-(6-methyl-1,2,4,5-tetrazin-3-yl)phenylalanine) (710 mg, 1.97 mmol) was dissolved in 1:1 DCM:HCl (~8 mL of each) and stirred at room temperature for 1 h. A pink precipitate formed almost immediately. This solvent was then removed in vacuo to afford the de-protected amino acid product. ESI-MS calc. for C$_{12}$H$_{14}$N$_5$O$_2$$^+$ 260.11; found 260.4.

Example 4. 2-(((((9H-Fluoren-9-yl)methoxy)carbonyl)amino)-3-(4-(6-methyl-1,2,4,5-tetrazin-3-yl)phenyl)propanoic acid (N-(((9H-Fluoren-9-yl)methoxy)carbonyl)-4-(6-methyl-1,2,4,5-tetrazin-3-yl) phenylalanine)

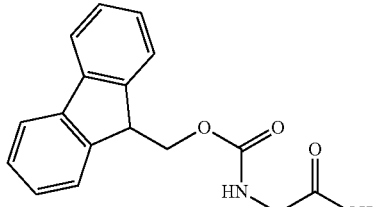

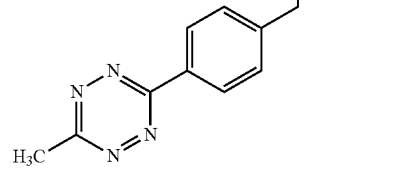

The dried product mix from the previous example was then dissolved in 1:1 MeOH:acetone (~50 mL of each) and Fmoc succinimidyl ester was added (3.3 g, 9.8 mmol) along with 0.55 mL TEA (3.9 mmol). The mixture was then stirred at room temperature for 2 h before the solvent was removed by rotary evaporation. The product was then purified by column chromatography, eluting with 10:1.5:0.1%, DCM: acetone:formic acid as a pinkish-red solid (76% yield from 2-((tert-Butoxycarbonyl)amino)-3-(4-(6-methyl-1,2,4,5-tetrazin-3-yl)phenyl)propanoic acid (N-(tert-butoxycarbonyl)-4-(6-methyl-1,2,4,5-tetrazin-3-yl)phenylalanine)). ESI-MS calc. for $C_{27}H_{24}N_5O_4^+$ 482.18; found 482.5. $^1$H NMR (DMSO-$d_6$) δ 12.84 (1 h, s), 8.37 (2H, d, J=8.5 Hz), 7.86 (2H, d, J=7.5 Hz), 7.81 (1H, d, J=8.5 Hz), 7.64 (2H, dd, J=7.0, 5.0 Hz), 7.55 (2H, d, J=8.5 Hz), 7.38 (2H, dd), 7.28 (2H, dd), 4.29 (1H, m), 4.21 (2H, d, J=7.5 Hz), 4.15 (1H, t, J=7.5 Hz), 3.22 (1H, dd, J=13.5, 4.5 Hz), 3.03-2.99 (4H, m).

Example 5. 6-(1,2,4,5-tetrazin-3-yl)nicotinic acid

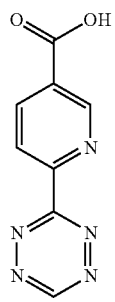

To a finely divided mixture of 6-cyanopyridine-3-carboxylic acid (2 mmol, 296 mg) and formamidine acetate (10 mmol, 1.04 g) was added hydrazine hydrate (2 mL) via syringe under an atmosphere of nitrogen. The resulting clear solution was then heated in an oil bath under a nitrogen atmosphere at 60° C. for 30 min. During this time, the solution turned yellow-orange in color. After cooling, the solution was acidified to pH 3 by addition of 5% aqueous HCl, resulting in formation of a yellow-orange precipitate. The precipitate was filtered and washed with water (3×10 mL), and dried to give 185 mg or solid containing the dihydrotetrazine intermediate. This solid was suspended in MeOH (25 mL) with sonication to give a suspension of finely divided particles. To this suspension was added solid tetrachloro-1,4-benzoquinone (1 mmol, 246 mg) and the suspension was stirred for 15 min. During this time, the tetrachloro-1,4-benzoquinone, and crude dihydrotetrazine intermediate go into solution and a new pink crystalline solid forms. The solution was filtered and washed with MeOH (2×5 mL) to give 6-(1,2,4,5-tetrazin-3-yl)nicotinic acid (49 mg). A second crop of product can be obtained by working up the filtrate from the oxidation step. First the filtrate is dried in vacuo, and then washed with dichloromethane (3×50 mL), allowing the solids to stir with the dichloromethane for 5 minutes for each wash. The remaining solids were then dried and extracted with ethyl acetate (4×20 mL), allowing the solids to stir with the ethyl acetate for 5 minutes for each wash. The last ethyl acetate filtrate only has a light pink color indicating the majority of the tetrazine has been extracted from the solids. The ethyl acetate washes were then combined and dried in vacuo to afford a second batch of product as a pink solid (40 mg), giving a combined yield of 89 mg (22%). HPLC analysis indicates the product is >90% pure. ESI-MS calc. for $C_8H_4N_5O_2^+$ 202.04; found 202.0. $^1$H NMR (DMSO-$d_6$) δ 13.8 (1H, br s), 10.75 (1H, s), 9.35 (1H, s), 8.67 (1H, d, J=8.0 Hz), 8.59 (1H, d, J=8.0).

Example 6. 5-(1,2,4,5-Tetrazin-3-yl)picolinic acid

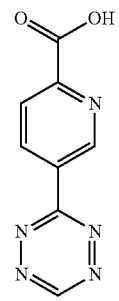 [SMILES: O=C(O)c1ccc(-c2nncnn2)cn1]

To a finely divided mixture of 6-cyanopyridine-3-carboxylic acid (2 mmol, 296 mg) and formamidine acetate (10 mmol, 1.04 g) was added hydrazine hydrate (2 mL) via syringe under an atmosphere of nitrogen. The resulting tan solution was then heated in an oil bath under a nitrogen atmosphere at 60° C. for 30 min. During this time, the reaction turned yellow-orange in color. After cooling, the solution was neutralized to pH 7 by addition of 5% aqueous HCl. Then NaNO$_2$ (10 mmol, 690 mg) in water (2 mL) was added. To this solution was slowly added 5% aqueous HCl until the pH of the solution reached 3. After allowing the reaction mixture to stir for approximately 15 min., a pink precipitate forms. The precipitate was isolated by filtration, washed with 0.1% aqueous HCl (3×10 ml) and dried in vacuo giving product (118 mg, 29%) that is >90% pure by HPLC without any additional purification. ESI-MS calc. for $C_8H_4N_5O_2^+$ 202.04; found 202.0. $^1$H NMR (DMSO-$d_6$) δ 10.71 (1H, s), 9.66 (1H, d, J=2.0 Hz), 8.93 (1H, dd, J=8.5, 2.0 Hz), 8.26 (1H, d, J=8.5).

Example 7.
2-Fluoro-4-(1,2,4,5-tetrazin-3-yl)benzoic acid

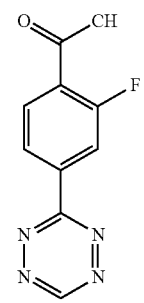 [SMILES: CC(=O)c1ccc(-c2nncnn2)cc1F]

To a finely divided mixture of 5-cyano-2-fluorobenzoic acid (2 mmol, 330 mg) and formamidine acetate (10 mmol, 1.04 g) was added hydrazine hydrate (2 mL) via syringe under an atmosphere of nitrogen. The resulting tan slurry was then heated in an oil bath under a nitrogen atmosphere at 60° C. for 30 min. During this time, all of the suspended dissolve leaving a yellow-orange solution. After cooling, the solution was neutralized to pH 7 by addition of 5% aqueous HCl. Then NaNO$_2$ (10 mmol, 690 mg) in water (2 mL) was added. To this solution was slowly added 5% aqueous HCl until the pH of the solution reached 3. During this addition, a pink precipitate forms. The precipitate was isolated by filtration, washed with 0.1% aqueous HCl (3×10 ml) and dried in vacuo giving product (109 mg, 25%) that is >90% pure by HPLC without any additional purification. ESI-MS calc. for $C_9H_4FN_4O_2^+$ 219.03; found 219.0. $^1$H NMR (DMSO-d$_6$) δ 13.63 (1H, br s), 10.69 (1H, s), 8.42 (1H, dd, J=8.5, 1.5 Hz), 8.32 (1H, dd, J=11.5, 1.5 Hz), 8.15 (1H, t, J=8.0).

The following additional Examples are prepared using methods analogous to those described herein or modifications thereof:

Example 8. 2-((tert-Butoxycarbonyl)amino)-3-(6-methyl-1,2,4,5-tetrazin-3-yl)propanoic acid (N-(tert-Butoxycarbonyl)-3-(6-methyl-1,2,4,5-tetrazin-3-yl)alanine)

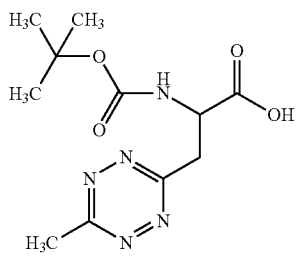 [SMILES: Cc1nnc(CC(NC(=O)OC(C)(C)C)C(=O)O)nn1]

This compound was prepared by the method of Example 2, using, e.g., 2-(tert-butoxycarbonyl)amino-3-cyanopropanoic acid and acetonitrile or acetamidine hydrochloride as starting materials and ZnCl$_2$ or zinc triflate catalyst. With 2-(tert-butoxycarbonyl)amino-3-cyanopropanoic acid, acetonitrile, and ZnCl$_2$ a yield of 19% was obtained. ESI-MS calc. for $C_{11}H_{16}N_5O_4^+$ 282.12; found 282.0. $^1$H NMR (DMSO-d$_6$) δ 12.87 (1H, br s), 7.26 (1H, d, J=8.5 Hz), 4.59 (1H, m), 3.69 (1H, dd, J=15.0, 6.0 Hz), 3.53 (1H, dd, J=14.5, 9.0 Hz), 2.95 (3H, s), 1.31 (9H, s).

Example 9.
3-(6-Methyl-1,2,4,5-tetrazin-3-yl)propanoic acid (3-(6-Methyl-1,2,4,5-tetrazin-3-yl)alanine)

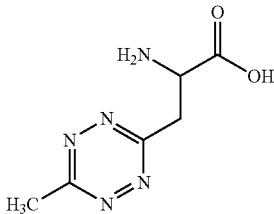

This compound is prepared by the method of Example 3 via deprotection of the compound of Example 8 under acidic conditions.

Example 10. 2-(((((9H-Fluoren-9-yl)methoxy)carbonyl)amino)-3-(6-methyl-1,2,4,5-tetrazin-3-yl)propanoic acid (N-(((9H-Fluoren-9-yl)methoxy)carbonyl)-3-(6-methyl-1,2,4,5-tetrazin-3-yl)alanine)

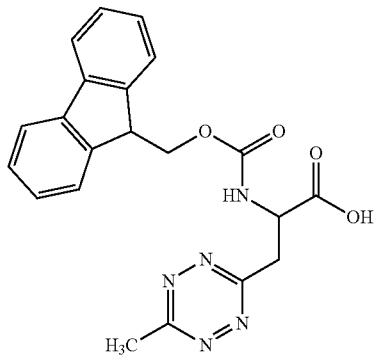 [SMILES: Cc1nnc(CC(NC(=O)OCC2c3ccccc3-c3ccccc32)C(=O)O)nn1]

This compound was prepared by the method analogous to Example 4 using the product of example 9 as starting material. ESI-MS calc. for $C_{21}H_{20}N_5O_4^+$ 406.15; found 406.3.

Example 11. 3-(1,2,4,5-Tetrazin-3-yl)propanoic acid

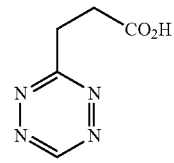 [SMILES: O=C(O)CCc1nncnn1]

This compound is prepared by the method of Example 2, using, e.g., 3-cyanopropanoic acid and formamidine acetate as starting materials and ZnCl$_2$ as catalyst.

Example 12.
3-(6-Methyl-1,2,4,5-tetrazin-3-yl)propanoic acid

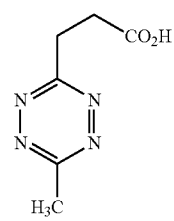

This compound was prepared by the method of Example 2, using, e.g., 3-cyanopropanoic acid and acetonitrile or acetamidine hydrochloride as starting materials and ZnCl$_2$ as catalyst. Using 3-cyanopropanoic acid and acetonitrile a yield of 25% was obtained. ESI-MS calc. for $C_6H_9N_4O_2^+$ 169.07; found 168.8. $^1$H NMR (DMSO-d$_6$) δ 3.46 (2H, t, J=7.0 Hz), 2.94 (3H, s), 2.91 (2H, t, J=7.0 Hz).

Example 13. 2,5-Dioxopyrrolidin-1-yl 3-(6-methyl-1,2,4,5-tetrazin-3-yl)propanoate

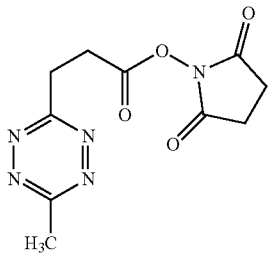 [SMILES: Cc1nnc(CCC(=O)ON2C(=O)CCC2=O)nn1]

To a solution of 3-(6-Methyl-1,2,4,5-tetrazin-3-yl)propanoic acid (145 mg, 0.86 mmol) in dimethylformamide (3.0 mL) was added N,N'-disuccinimidyl carbonate (884 mg, 3.45 mmol) and diisopropylethylamine (700 µL). The reaction mixture was allowed to stir at room temperature for 1 h. The product was purified by preparative HPLC. ESI-MS calc. for $C_{10}H_{12}N_5O_4^+$ 266.09; found 266.0.

Example 14. 2,5-Dioxopyrrolidin-1-yl 3-(1,2,4,5-tetrazin-3-yl)propanoate

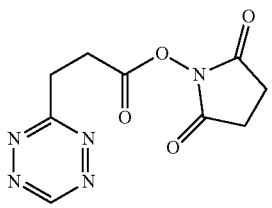 [SMILES: O=C(CCc1nncnn1)ON1C(=O)CCC1=O]

This compound is prepared starting from the compound of Example 11 via the method of Example 13 by reaction with N,N' disuccinimidyl carbonate or by with N-hydroxysuccinimide in the presence of a suitable coupling agent.

Example 15. 2-((tert-Butoxycarbonyl)amino)-3-(4-(1,2,4,5-tetrazin-3-yl)phenyl)propanoic acid (N-(tert-Butoxycarbonyl)-4-(1,2,4,5-tetrazin-3-yl)phenylalanine)

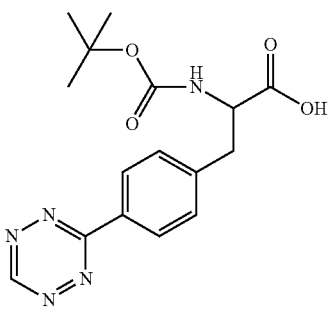 [SMILES: CC(C)(C)OC(=O)NC(Cc1ccc(-c2nncnn2)cc1)C(=O)O]

This compound is prepared by the method of Example 2, using, e.g., 2-((tert-butoxycarbonyl)amino)-3-(4-cyanophenyl)propanoic acid (N-(tert-butoxycarbonyl)-4-cyaanophenylalanine) and formamidine acetate as starting materials.

Example 16. 2-Amino-3-(4-(1,2,4,5-tetrazin-3-yl)phenyl)propanoic acid (4-(1,2,4,5-Tetrazin-3-yl)phenylalanine)

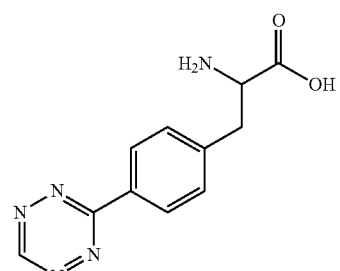

This compound is prepared by a method analogous to Example 3 using the compound of Example 14 as a starting material.

Example 17. 2-((((9H-Fluoren-9-yl)methoxy)carbonyl)amino)-3-(4-(1,2,4,5-tetrazin-3-yl)phenyl)propanoic acid (N-(((9H-Fluoren-9-yl)methoxy)carbonyl)-4-(1,2,4,5-tetrazin-3-yl) phenylalanine)

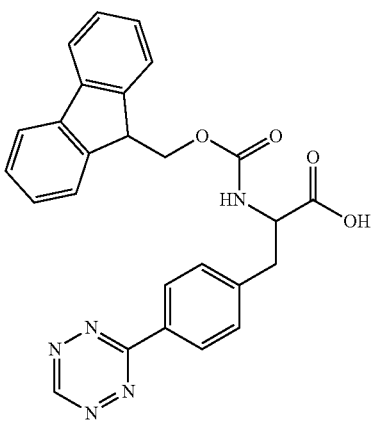 [SMILES: O=C(NC(Cc1ccc(-c2nncnn2)cc1)C(=O)O)OCC1c2ccccc2-c2ccccc21]

This compound is prepared by a method analogous to Example 4 using the compound of Example 15 as a starting material.

Example 18. 2-((tert-Butoxycarbonyl)amino)-3-(1,2, 4,5-tetrazin-3-yl)propanoic acid (N-(tert-Butoxycarbonyl)-3-(6-methyl-1,2,4,5-tetrazin-3-yl)alanine)

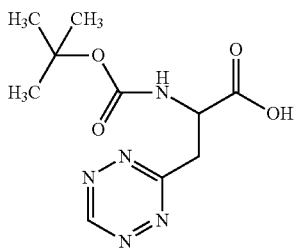 [SMILES: CC(C)(C)OC(=O)NC(Cc1nncnn1)C(=O)O]

This compound is prepared by the method of Example 2, using, e.g., 2-(tert-butoxycarbonyl)amino-3-cyanopropanoic acid and formamidine acetate as starting materials.

Example 19. 3-(1,2,4,5-Tetrazin-3-yl)propanoic acid (3-(6-Methyl-1,2,4,5-tetrazin-3-yl)alanine)

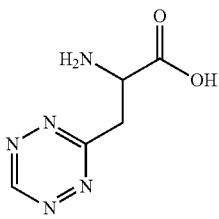 [SMILES: NC(Cc1nncnn1)C(=O)O]

This compound is prepared from the compound of Example 17 by the method of Example 3, using deprotection under acidic conditions.

Example 20. 2-(((((9H-Fluoren-9-yl)methoxy)carbonyl)amino)-3-(1,2,4,5-tetrazin-3-yl)propanoic acid (N-(((9H-Fluoren-9-yl)methoxy)carbonyl)-3-(1,2,4, 5-tetrazin-3-yl)alanine)

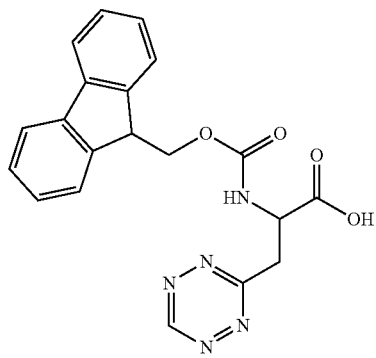 [SMILES: O=C(NC(Cc1nncnn1)C(=O)O)OCC1c2ccccc2-c2ccccc21]

This compound is prepared from the compound of Example 18, using a method analogous to that described in Example 4.

Example 21. 2-(6-Methyl-1,2,4,5-tetrazin-3-yl)ethyl 4-methylbenzenesulfonate

Step 1. 2-(1,2,4,5-tetrazin-3-yl)ethanol

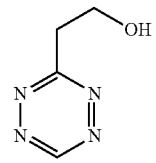

To a mixture of ethyl 3-hydroxypropanimidate hydrochloride (1 mmol, 153 mg) and formamidine acetate (5 mmol, 521 mg) was added hydrazine hydrate (1 mL) under an atmosphere of argon. After stirring at room temperature for 2 hours, the mixture was diluted with water (10 mL) and sodium nitrite (12.5 mmol, 0.86 g) was added. To this solution was added 2% aqueous HCl dropwise on an ice bath until the now pink solution reached a pH of 3. The aqueous solution was extracted with methylene chloride (5×25 mL), dried with magnesium sulfate, the solvent was removed by rotary evaporation, and then dried under vacuum to afford the product, 2-(1,2,4,5-tetrazin-3-yl)ethanol (28 mg, 22%), as a pink oil. ESI-MS calc. for $C_4H_7N_4O^+$: 127.06, found: 126.7.

Step 2. 2-(6-Methyl-1,2,4,5-tetrazin-3-yl)ethyl 4-methylbenzenesulfonate

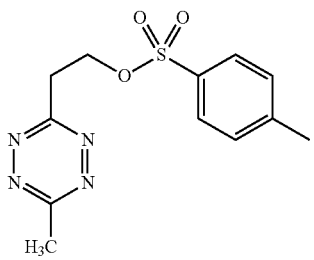 [SMILES: Cc1ccc(S(=O)(=O)OCCc2nnc(C)nn2)cc1]

This compound is prepared 2-(1,2,4,5-tetrazin-3-yl)ethanol with p-toluenesulfonyl chloride, e.g., in the presence of pyridine.

Example 22. 6-(3-(1,2,4,5-Tetrazin-3-yl)propanamido)-2-((tert-butoxycarbonyl)amino)hexanoic acid (6-N-(3-(1,2,4,5-Tetrazin-3-yl)propanoyl)-2-N-(tert-butoxycarbonyl)lysine)

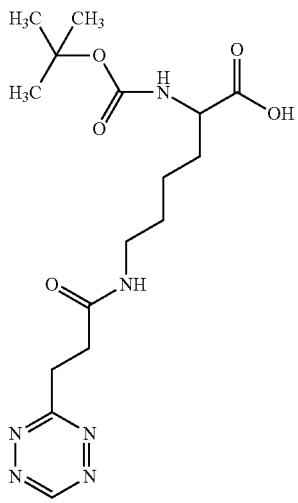 [SMILES: CC(C)(C)OC(=O)NC(CCCCNC(=O)CCc1nncnn1)C(=O)O]

This compound is prepared starting from the compound of Example 14 by reaction with 2-N-(tert-butyloxycarbonyl) lysine.

Example 23. 6-(3-(1,2,4,5-Tetrazin-3-yl)propanamido)-2-aminohexanoic acid (6-N-(3-(1,2,4,5-Tetrazin-3-yl)propanoyl)lysine)

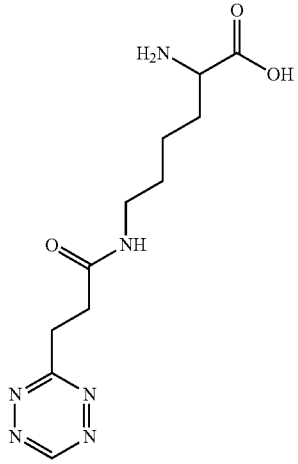 [SMILES: NC(CCCCNC(=O)CCc1nncnn1)C(=O)O]

This compound is prepared starting from the compound of Example 22 by deprotection under acidic conditions.

Example 24. 6-(3-(1,2,4,5-Tetrazin-3-yl)propanamido)-2-((((9H-fluoren-9-yl)methoxy)carbonyl)amino)hexanoic acid (2-N-(((9H-Fluoren-9-yl)methoxy)carbonyl)-(6-N-(3-(1,2,4,5-tetrazin-3-yl)propanoyl)lysine)

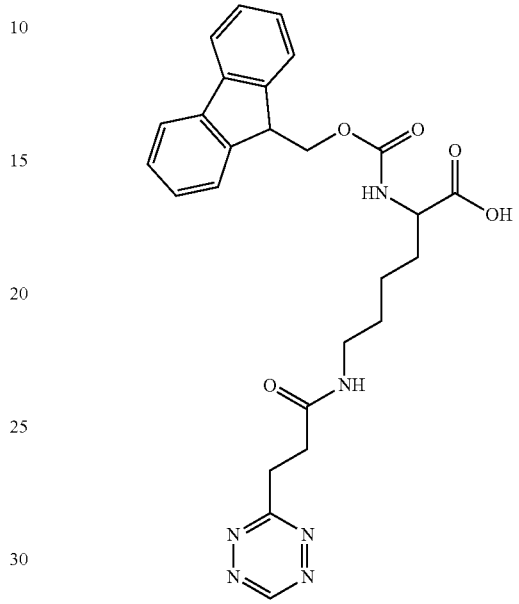

This compound is prepared starting from the compound of Example 14 by reaction with α-Fmoc-L-Lysine hydrochloride.

Example 25. 6-(3-(6-Methyl-1,2,4,5-tetrazin-3-yl)propanamido)-2-((tert-butoxycarbonyl)amino)hexanoic acid (6-N-(3-(6-Methyl-1,2,4,5-tetrazin-3-yl)propanoyl)-2-N-(tert-butoxycarbonyl)lysine)

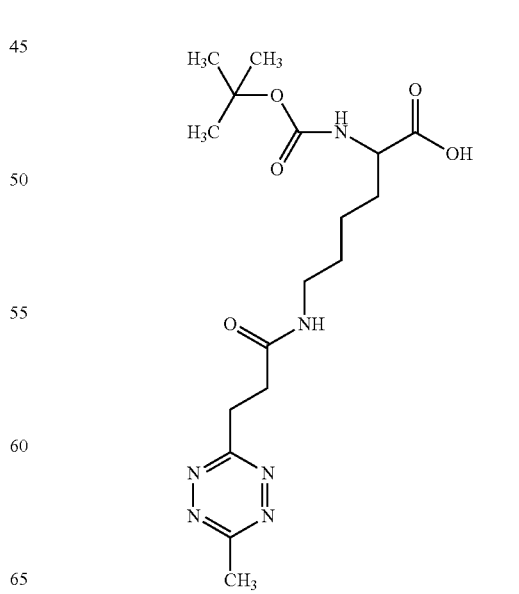

This compound was prepared starting from the compound of Example 13 by reaction with 2-N-(tert-butyloxycarbonyl) lysine. ESI-MS calc. for $C_{17}H_{29}N_6O_5^+$ 397.22; found 397.2. $^1$H NMR (D$_2$O) δ 4.05 (1H, m), 3.62 (2H, t, J=7.0 Hz), 3.17 (2H, t, J=7.0 Hz), 3.03 (3H, s), 2.92 (2H, t, J=6.5 Hz), 1.75-1.3 (15H, m).

Example 26. 6-(3-(6-Methyl-1,2,4,5-tetrazin-3-yl) propanamido)-2-aminohexanoic acid (6-N-(3-(6-Methyl-1,2,4,5-tetrazin-3-yl)propanoyl) lysine)

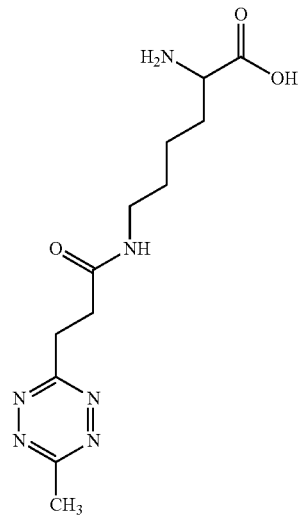 [SMILES: Cc1nnc(CCC(=O)NCCCCC(N)C(=O)O)nn1]

This compound is prepared starting from the compound of Example 25 by deprotection under acidic conditions.

Example 27. 6-(3-(6-Methyl-1,2,4,5-tetrazin-3-yl) propanamido)-2-((((9H-fluoren-9-yl)methoxy)carbonyl)amino)hexanoic acid (2-N-(((9H-Fluoren-9-yl)methoxy)carbonyl)-(6-N-(3-(6-methyl-1,2,4,5-tetrazin-3-yl)propanoyl)lysine)

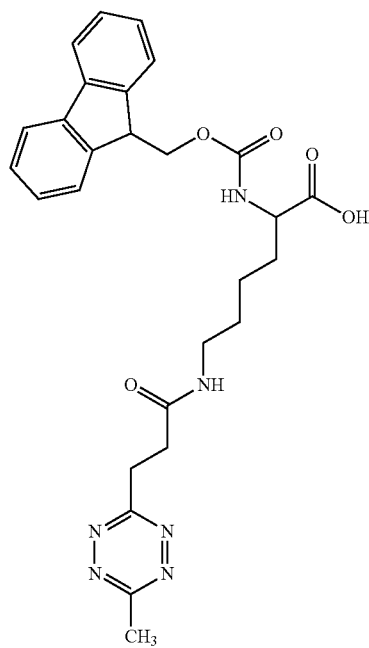 [SMILES: Cc1nnc(CCC(=O)NCCCCC(NC(=O)OCC2c3ccccc3-c3ccccc32)C(=O)O)nn1]

This compound was prepared starting from the compound of Example 12 by reaction with α-Fmoc-L-Lysine hydrochloride in the presence of N,N'-dicyclohexylcarbodiimide and 1-hydroxybenzotriazole hydrate in dimethylformamide. ESI-MS calc. for $C_{27}H_{31}N_6O_5^+$ 519.24; found 519.4. $^1$H NMR (DMSO-d$_6$) δ 7.97 (1H, t), 7.89 (2H, d), 7.72 (2H, d), 7.60 (1H, d), 7.41 (2H, t), 7.32 (2H, t), 4.28 (2H, d), 4.22 (1H, t), 3.91 (1H, m), 3.44 (2H, t), ~3.0 (2H overlapping water peak), 2.92 (3H, s), 2.75 (2H, t), 1.7-1.25 (6H, m).

Example 28. 2,5-dioxopyrrolidin-1-yl (2-(1,2,4,5-tetrazin-3-yl)ethyl) carbonate

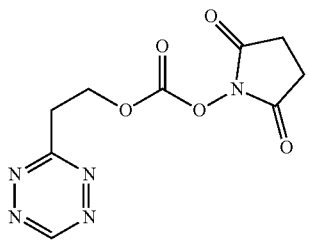 [SMILES: O=C(OCCc1nncnn1)ON1C(=O)CCC1=O]

This compound is prepared reacting 2-(1,2,4,5-tetrazin-3-yl)ethanol (see Example 21, step 1) with disuccinimidyl carbonate.

Example 29. 2,5-dioxopyrrolidin-1-yl (2-(6-methyl-1,2,4,5-tetrazin-3-yl)ethyl) carbonate Step 1. 2-(6-Methyl-1,2,4,5-tetrazin-3-yl)ethanol

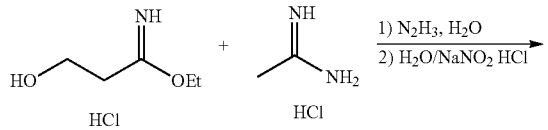

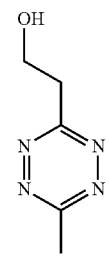

To a mixture of ethyl 3-hydroxypropanimidate hydrochloride (2 mmol, 307 mg) and acetamidine hydrochloride (10 mmol, 945 mg) was added hydrazine hydrate (2 mL) under an atmosphere of argon. After stirring at room temperature for 2 hours, the mixture was diluted with water (25 mL) and sodium nitrite (25 mmol, 1.72 g) was added. To this solution was added 2% aqueous HCl dropwise on an ice bath until the now pink solution reached a pH of 3. The aqueous solution was extracted with methylene chloride (5×50 mL), dried with magnesium sulfate, the solvent was removed by rotary evaporation, and then dried under vacuum to afford the product, 2-(6-methyl-1,2,4,5-tetrazin-3-yl)ethanol (140 mg, 37%), as a pink oil. ESI-MS calc. for $C_5H_9N_4O^+$: 141.08, found: 140.7.

Step 2. 2,5-dioxopyrrolidin-1-yl (2-(6-methyl-1,2,4,5-tetrazin-3-yl)ethyl) carbonate

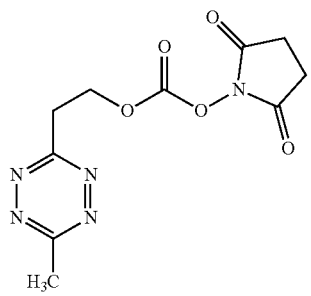 [SMILES: Cc1nnc(CCOC(=O)ON2C(=O)CCC2=O)nn1]

The compound is prepared by the method of Example 2, using e.g., 3-hydroxypropionitrile and acetonitrile or acetamidine as starting materials followed by reaction of the resulting 3-(2-hydroxyethyl)-6-methyl-1,2,4,5-tetrazine with disuccinimidyl carbonate.

Example 30. 2-Amino-6-(((2-(1,2,4,5-tetrazin-3-yl)ethoxy)carbonyl)amino)hexanoic acid (6-N-((2-(1,2,4,5-Tetrazin-3-yl)ethoxy)carbonyl)lysine)

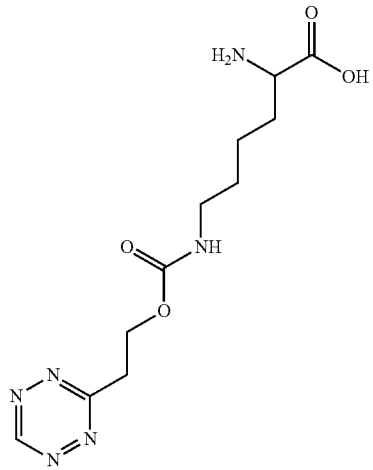 [SMILES: NC(CCCCNC(=O)OCCc1nncnn1)C(=O)O]

This compound is prepared from the compound of Example 28 by the reaction of a 2-amino-protected (e.g., BOC-protected) lysine, followed by deprotection (e.g., under acidic conditions).

Example 31. 2-Amino-6-(((2-(6-methyl-1,2,4,5-tetrazin-3-yl)ethoxy)carbonyl)amino)hexanoic acid (6-N-((2-(6-Methyl-1,2,4,5-tetrazin-3-yl)ethoxy)carbonyl)lysine)

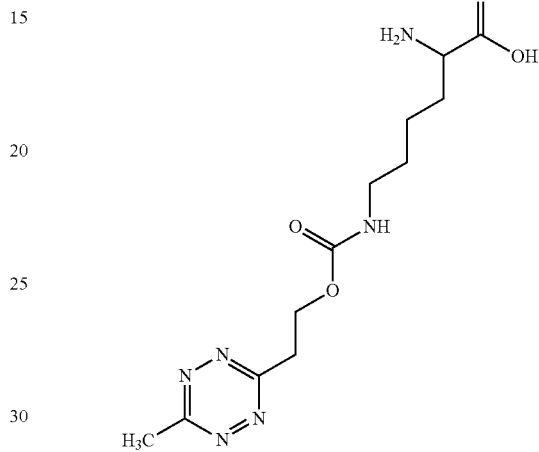

This compound is prepared from the compound of Example 29 by the reaction of a 2-amino-protected (e.g., BOC-protected) lysine, followed by deprotection (e.g., under acidic conditions).

Example 32. 2-Amino-5-((5-(1,2,4,5-tetrazin-3-yl)pentyl)amino)-5-oxopentanoic acid (5-N-(5-(1,2,4,5-Tetrazin-3-yl)pentyl)glutamine)

Step 1. 5-(1,2,4,5-Tetrazin-3-yl)pentan-1-amine hydrochloride

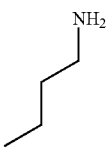

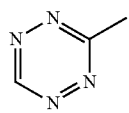

To a mixture of ethyl 6-aminohexanimidate dihydrochloride (2 mmol, 462 mg) and formamidine acetate (10 mmol, 1.04 g) was added hydrazine hydrate (2 mL) under an atmosphere of argon. After stirring at room temperature for 2 hours, the mixture was diluted with water (25 mL) and sodium nitrite (25 mmol, 1.72 g) was added. To this solution was added 2% aqueous HCl dropwise on an ice bath until the pink solution reached a pH of 3. The solvent was removed by rotary evaporation and the residue was washed with methanol (2×25 mL). After filtration, the remaining solid was dissolved in water (25 mL) and saturated with solid Na$_2$CO$_3$. This solution was extracted with methylene chloride (4×25 mL). To the pink organic solution was added 250 μL TFA and the solvent was removed by rotary evaporation. Preparative HPLC using an isocratic gradient of 100% buffer A (buffer A is water with 0.1% TFA) afforded the trifluoroacetate salt of the tetrazine. This material was then loaded on a reverse phase C18 column, washed with 0.1% aqueous HCl, and eluted with a 1:1 mixture of methanol and 0.1% aqueous HCl to afford pure 5-(1,2,4,5-tetrazin-3-yl)pentan-1-amine hydrochloride (55 mg, 13.5%), as a pink solid. ESI-MS calc. for C$_7$H$_{14}$N$_5$$^+$ 168.12, found: 167.8.

Step 2. 2-Amino-5-((5-(1,2,4,5-tetrazin-3-yl)pentyl)amino)-5-oxopentanoic acid (5-N-(5-(1,2,4,5-Tetrazin-3-yl)pentyl)glutamine)

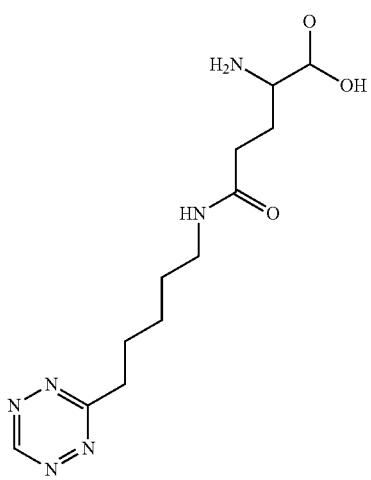 [SMILES: NC(CCC(=O)NCCCCCc1nncnn1)C(O)O]

This compound is prepared by coupling of 5-(1,2,4,5-tetrazin-3-yl)pentylamine hydrochloride from Step 1 with an appropriately protected glutamic acid derivative, such as N-BOC-glutamic acid tert-butyl ester, followed by deprotection (e.g., under acidic conditions).

Example 33. 2-Amino-5-((5-(6-methyl-1,2,4,5-tetrazin-3-yl)pentyl)amino)-5-oxopentanoic acid (5-N-(5-(6-Methyl-1,2,4,5-tetrazin-3-yl)pentyl)glutamine)

Step 1.
5-(6-Methyl-1,2,4,5-tetrazin-3-yl)pentan-1-amine hydrochloride

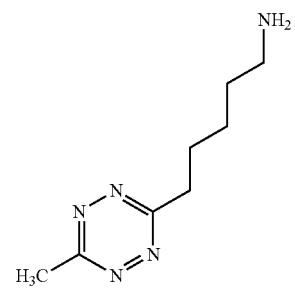

To a mixture of ethyl 6-aminohexanimidate dihydrochloride (2 mmol, 462 mg) and acetamidine hydrochloride (10 mmol, 945 mg) was added hydrazine hydrate (2 mL) under an atmosphere of argon. After stirring at room temperature for 2 hours, the mixture was diluted with water (25 mL) and sodium nitrite (25 mmol, 1.72 g) was added. To this solution was added 2% aqueous HCl dropwise on an ice bath until the pink solution reached a pH of 3. The aqueous solution was then basified to pH 12 by dropwise addition of 10% aqueous NaOH on an ice bath. The basic solution was extracted with methylene chloride (4×25 mL), dried with magnesium sulfate, and the solvent was removed by rotary evaporation. Preparative HPLC using a gradient of 0 to 25% buffer B (buffer A is water with 0.1% TFA, and buffer B is acetonitrile with 10% water and 0.1% TFA) afforded the trifluoroacetate salt of the tetrazine. This material was then loaded on a reverse phase C18 column, washed with 0.1% aqueous HCl, and eluted with a 1:1 mixture of methanol and 0.1% aqueous HCl to afford pure 5-(6-methyl-1,2,4,5-tetrazin-3-yl)pentan-1-amine hydrochloride (100 mg, 23%), as a pink solid. ESI-MS calc. for C$_8$H$_{16}$N$_5$$^+$182.14, found: 182.0.

Step 2. 2-Amino-5-((5-(6-methyl-1,2,4,5-tetrazin-3-yl)pentyl)amino)-5-oxopentanoic acid (5-N-(5-(6-Methyl-1,2,4,5-tetrazin-3-yl)pentyl)glutamine)

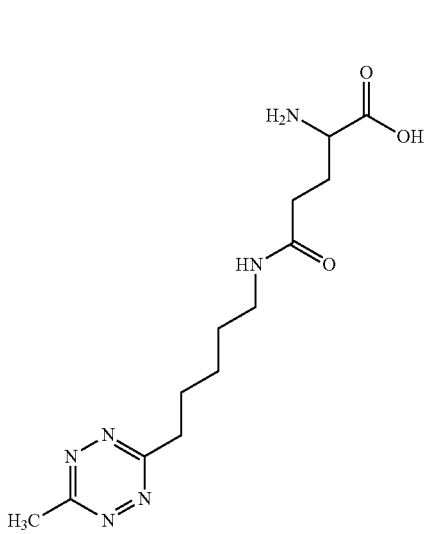 [SMILES: Cc1nnc(CCCCCNC(=O)CCC(N)C(=O)O)nn1]

This compound is prepared by coupling of 5-(6-methyl-1,2,4,5-tetrazin-3-yl)pentan-1-amine hydrochloride from Step 1 with an appropriately protected glutamic acid derivative, such as N-BOC-glutamic acid tert-butyl ester, followed by deprotection (e.g., under acidic conditions).

Example 34. 2-Amino-6-(4-(1,2,4,5-tetrazin-3-yl)benzamido)hexanoic acid (6-(4-(1,2,4,5-Tetrazin-3-yl)benzoyl)lysine)

Step 1. 4-(1,2,4,5-Tetrazin-3-yl)benzoic acid

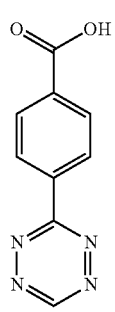

4-(1,2,4,5-Tetrazin-3-yl)benzoic acid is prepared from 4-cyanobenzoic acid and formamidine acetate by a method analogous to that described in Example 6. $^1$H NMR (500 MHz, DMSO-$d_6$) δ 8.22 (2H, d, J=8.0 Hz), 8.62 (2H, d, J=8.5 Hz), 10.66 (1H, s) HRMS-ESI [M-H]$^-$ m/z calc. for $C_9H_5N_4O_2^-$ 201.0418, found 201.0416.

Step 2. 6-(4-(1,2,4,5-Tetrazin-3-yl)benzamido)-2-((tert-butoxycarbonyl)amino)hexanoic acid

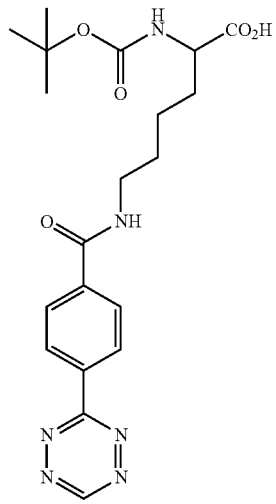 [SMILES: CC(C)(C)OC(=O)NC(CCCCNC(=O)c1ccc(-c2nncnn2)cc1)C(=O)O]

This compound is prepared by activation of 4-(1,2,4,5-tetrazin-3-yl)benzoic acid from Step 1\in the presence of N-(3-dimethylaminopropyl)-N'-ethylcarbodiimide hydrochloride and 1-hydroxybenzotriazole hydrate followed by addition of an appropriately protected lysine derivative, such as N-BOC-L-lysine. 6-(4-(1,2,4,5-Tetrazin-3-yl)benzamido)-2-((tert-butoxycarbonyl)amino)hexanoic acid (50% yield) is obtained after HPLC purification. ESI-MS calc. for $C_{20}H_{27}N_6O_5^+$ 431.20; found 431.2.

Step 3. 2-Amino-6-(4-(1,2,4,5-tetrazin-3-yl)benzamido)hexanoic acid (6-(4-(6-1,2,4,5-Tetrazin-3-yl)benzoyl)lysine)

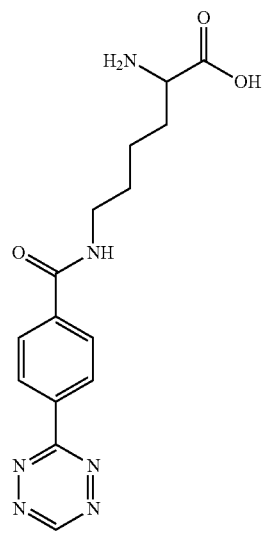 [SMILES: NC(CCCCNC(=O)c1ccc(-c2nncnn2)cc1)C(=O)O]

This compound is prepared by deprotection of the compound from Step 2 (e.g., under acidic conditions).

Example 35. 2-Amino-6-(4-(6-methyl-1,2,4,5-tetrazin-3-yl)benzamido)hexanoic acid (6-(4-(6-Methyl-1,2,4,5-tetrazin-3-yl)benzoyl)lysine)

Step 1. 4-(6-Methyl-1,2,4,5-Tetrazin-3-yl)benzoic acid

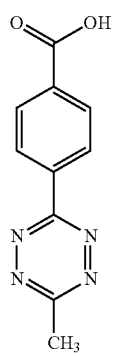

4-(6-Methyl-1,2,4,5-tetrazin-3-yl)benzoic acid is prepared from 4-cyanobenzoic acid and acetamidine hydrochloride by a method analogous to that described in Example 6. $^1$H NMR (500 MHz, DMSO-$d_6$) 3.03 (3H, s), 8.20 (2H, d, J=9.0 Hz), 8.58 (2H, d, J=8 Hz) HRMS-ESI [M-H]$^-$ calc. for [$C_{10}H_7N_4O_2$]$^-$ 215.0574, found 215.0574.

Step 2. 2-Amino-6-(4-(6-methyl-1,2,4,5-tetrazin-3-yl)benzamido)hexanoic acid (6-(4-(6-methyl-1,2,4,5-tetrazin-3-yl)benzoyl)lysine)

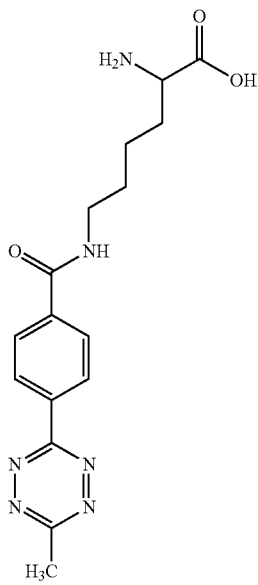 [SMILES: Cc1nnc(-c2ccc(C(=O)NCCCCC(N)C(=O)O)cc2)nn1]

This compound is prepared by coupling of 4-(6-methyl-1,2,4,5-tetrazin-3-yl)benzoic acid from Step 1 with an appropriately protected lysine derivative, such as N-BOC-lysine tert-butyl ester, followed by deprotection (e.g., under acidic conditions).

Example 36. 2-((((9H-Fluoren-9-yl)methoxy)carbonyl)amino)-6-(4-(6-methyl-1,2,4,5-tetrazin-3-yl)benzamido)hexanoic acid

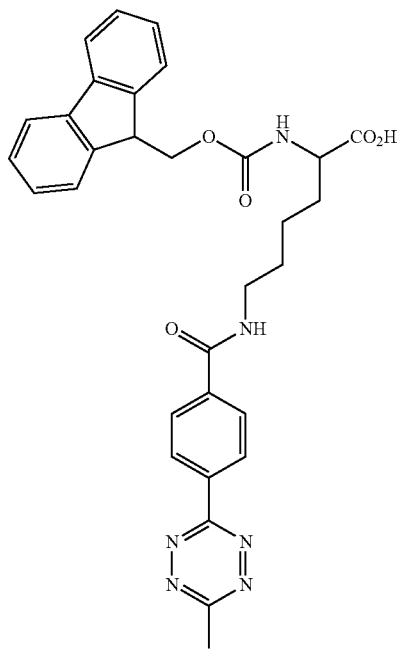 [SMILES: Cc1nnc(-c2ccc(C(=O)NCCCCC(NC(=O)OCC3c4ccccc4-c4ccccc43)C(=O)O)cc2)nn1]

This compound is prepared by activation of 4-(6-methyl-1,2,4,5-tetrazin-3-yl)benzoic acid from Example 25, Step 1 in the presence of N,N'-dicyclohexylcarbodiimide and 1-hydroxybenzotriazole hydrate followed by addition of an appropriately protected lysine derivative, such as N$_\alpha$-Fmoc-L-lysine. 2-((((9H-Fluoren-9-yl)methoxy)carbonyl)amino)-6-(4-(6-methyl-1,2,4,5-tetrazin-3-yl)benzamido)hexanoic acid is obtained after HPLC purification. ESI-MS calc. for $C_{31}H_{31}N_6O_5^+$ 567.24; found 567.4.

Example 37. 2-(1,2,4,5-Tetrazin-3-yl)acetic acid

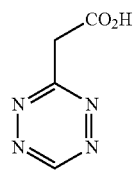

This compound is prepared by the method of Example 1, using, e.g., cyanoacetic acid and formamidine as starting materials.

Example 38.
2-(6-Methyl-1,2,4,5-tetrazin-3-yl)acetic acid

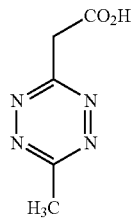

This compound is prepared by the method of Example 1, using, e.g., cyanoacetic acid and acetamidine or acetonitrile as starting materials.

All publications, patent applications, patents and other references mentioned herein, throughout the entire disclosure, are hereby incorporated by reference in their entirety.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound according to the Formula (III):

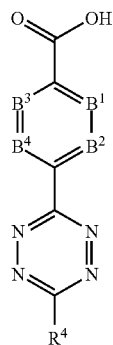

(III)

or a salt thereof, wherein:
$R^4$ is hydrogen, $(C_1-C_6)$alkyl, or substituted $(C_1-C_6)$alkyl;
$B^1$ is N, $B^2$ is CH, $B^3$ is N or CH, and $B^4$ is N or CH; or
$B^1$ is CH, $B^2$ is N, $B^3$ is N or CH, and $B^4$ is N or CH; or
$B^1$ is CH or $CR^5$, $B^2$ is CH or $CR^5$, $B^3$ is CH or $CR^5$ and $B^4$ is CH or $CR^5$; and
each $R^5$ is halogen, nitro or $CF_3$;
provided that
no more than two of $B^1$, $B^2$, $B^3$ and $B^4$ are N; and
no more than three of $B^1$, $B^2$, $B^3$ and $B^4$ are CH.

2. A compound or salt thereof according to claim 1, wherein $R^4$ is hydrogen, $(C_1-C_6)$alkyl or $(C_1-C_6)$haloalkyl.
3. A compound or salt thereof according to claim 1, wherein $R^4$ is hydrogen.
4. A compound or salt thereof according to claim 1, wherein $R^4$ is $(C_1-C_6)$alkyl.
5. A compound or salt thereof according to claim 4, wherein $R^4$ is methyl.
6. A compound or salt thereof according to claim 1, wherein $B^1$ is N, $B^2$ is CH, $B^3$ is CH and $B^4$ is CH.
7. A compound or salt thereof according to claim 1, wherein $B^1$ is N, $B^2$ is CH, $B^3$ is N and $B^4$ is CH.
8. A compound or salt thereof according to claim 1, wherein $B^1$ is N, $B^2$ is CH, $B^3$ is CH and $B^4$ is N.
9. A compound or salt thereof according to claim 1, wherein $B^1$ is CH, $B^2$ is N, $B^3$ is CH and $B^4$ is CH.
10. A compound or salt thereof according to claim 1, wherein $B^1$ is CH, $B^2$ is N, $B^3$ is CH and $B^4$ is N.
11. A compound or salt thereof according to claim 1, wherein $B^1$ is CH or $CR^5$, $B^2$ is CH or $CR^5$, $B^3$ is CH or $CR^5$ and $B^4$ is CH or $CR^5$.
12. A compound or salt thereof according to claim 1, wherein $B^1$ is $CR^5$, $B^2$ is CH, $B^3$ is CH and $B^4$ is CH.
13. A compound or salt thereof according to claim 1, wherein $R^5$ is halogen.
14. A compound or salt thereof according to claim 13, wherein $R^5$ is fluorine.
15. A compound or salt thereof according to claim 1, wherein the compound is selected from compounds of the following formulae:

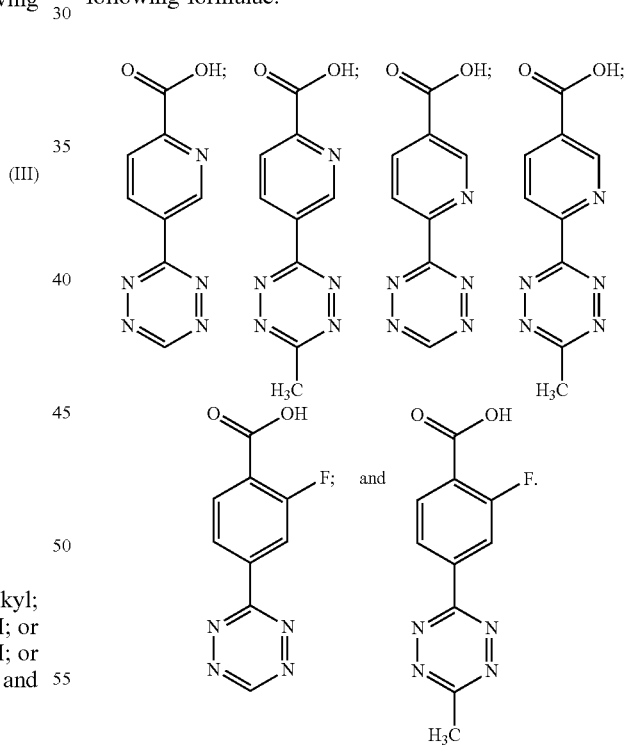

* * * * *